United States Patent
Slocum et al.

(10) Patent No.: US 10,053,798 B2
(45) Date of Patent: Aug. 21, 2018

(54) METHODS AND SYSTEMS FOR MANUFACTURING A TABLET

(71) Applicant: Massachusetts Institute of Technology, Cambridge, MA (US)

(72) Inventors: Alexander H. Slocum, Bow, NH (US); Nicholas M. Sondej, Guilford, CT (US); Bernhardt Levy Trout, Lexington, MA (US); Gregory C. Rutledge, Newton, MA (US); Indrani Bhattacharyya, Quincy, MA (US)

(73) Assignee: Massachusetts Insititute of Technology, Cambridge, MA (US)

( * ) Notice: Subject to any disclaimer, the term of this patent is extended or adjusted under 35 U.S.C. 154(b) by 407 days.

(21) Appl. No.: 14/701,218

(22) Filed: Apr. 30, 2015

(65) Prior Publication Data
US 2016/0319464 A1 Nov. 3, 2016

(51) Int. Cl.
| B05B 5/025 | (2006.01) |
| D01D 5/00 | (2006.01) |
| A61J 3/00 | (2006.01) |
| A61K 9/20 | (2006.01) |
| A61J 3/10 | (2006.01) |

(52) U.S. Cl.
CPC .............. *D01D 5/0076* (2013.01); *A61J 3/00* (2013.01); *A61K 9/2095* (2013.01); *B05B 5/025* (2013.01); *A61J 3/10* (2013.01)

(58) Field of Classification Search
USPC ......... 118/620–640, 326, 309, 325, 307, 317
See application file for complete search history.

(56) References Cited

U.S. PATENT DOCUMENTS

| 1,975,504 | A | | 10/1934 | Formhals | |
| 2,109,333 | A | | 2/1938 | Formhals | |
| 3,068,516 | A | | 12/1962 | Hofer | |
| 3,920,099 | A | * | 11/1975 | Pondelicek | B22D 17/2007 118/317 |
| 4,393,809 | A | * | 7/1983 | Hilker | H01B 13/065 118/101 |
| 4,611,748 | A | | 9/1986 | Winter et al. | |
| 5,014,404 | A | | 5/1991 | Smith | |

(Continued)

OTHER PUBLICATIONS

Brettman, Electrospinning for Pharmaceutical Applications. MIT: Dept of Engineering. Date of Receipt: May 3, 2012. 3-149. Received by the MIT Library Jul. 19, 2012.

(Continued)

*Primary Examiner* — Yewebdar T Tadesse
(74) *Attorney, Agent, or Firm* — Wolf, Greenfield & Sacks, P.C.

(57) ABSTRACT

Methods and systems for manufacturing a tablet are generally provided. Certain embodiments comprise electrodepositing (e.g., electrospinning) a material (e.g., the tablet material, for example, within a fluid) onto a substrate. The substrate can be, for example, an elongated rod. In some such embodiments, after material has been electrodeposited onto the substrate, a die comprising a cavity and the substrate can be moved relative to each other such that the electrodeposited material is at least partially stripped from the substrate and/or at least partially deposited into the cavity of the die. Some embodiments comprise compressing the material in the cavity to form a tablet.

18 Claims, 18 Drawing Sheets

(56) References Cited

U.S. PATENT DOCUMENTS

| | | | |
|---|---|---|---|
| 5,865,979 | A | 2/1999 | Collins et al. |
| 7,799,261 | B2 | 9/2010 | Orr et al. |
| 2009/0208665 | A1* | 8/2009 | Eriksson .................. C23C 2/20 427/547 |
| 2009/0285999 | A1* | 11/2009 | Achtner ................ C23C 14/042 427/470 |
| 2011/0036723 | A1 | 2/2011 | Song |
| 2013/0295143 | A1 | 11/2013 | Trout et al. |

OTHER PUBLICATIONS

Deitzel et al., The effect of processing variables on the morphology of electrospun nanofibers and textiles. Polymer. 2001. 42: 260-72.

Katta et al., Continuous Electrospinning of Aligned Polymer Nanofibers onto a Wire Drum Collector. Nano Letters. 2004. 4(1): 2215-8.

Shin et al., Experimental characterization of electrospinning: the electrically forced jet and instabilities. Polymer. 2001. 42: 9955-67.

Subbiah et al., Electrospinning of Nanofibers. J of Applied Polymer Science. 2005. 96: 557-69. DOI 10.1002/app.21481.

Theron et al., Multiple jets in electrospinning: experiment and modeling. Polymer. Mar. 5, 2005. 46: 2889-2899.

Yang et al., A Shield Ring Enhanced Equilateral Hexagon Distributed Multi-needle Electrospinning Spinneret. IEEE. Oct. 2010. 17(5): 1592-1601.

Yarin et al., Bending instability in electrospinning of nanofibers. J of Applied Physics. Mar. 1, 2001. 89(5): 3018-26.

[No Author Listed] Alloy 6061: Understanding Extruded Aluminum Alloys. Alcoa Engineered Products. 2002. 2 pgs.

[No Author Listed] Investigation into the Impact of Air Pressure Driven Drug Dispensing Machines on the Environment of Pharmacy Workers: Results in Two U.S. Pharmacies—McKesson/Parata Max. AlburtyLab, Inc.: Reliable Aersol Science and Engineering. Jan. 6, 2009. 6 pages.

[No Author Listed] Laplace-Young and Bashforth-Adams Equations. Application Notes. First Ten Angstroms. Nov. 24, 2000. 2 pages.

[No Author Listed] Left, Right, Up, Down Contact Angles. First Ten Angstroms. Accessed Mar. 26, 2013. 3 pages. www.first-tenangstroms.com/faq/LeftRightUpDownContactAngles.html.

Bashforth et al. An attempt to test the theories of capillary action. Cambridge: At the University Press.1883. 147 pages.

Boucher et al., Pendent Drop Profiles and Related Capillary Phenomena. Proceedings of the Royal Society of London. A. Mathematical and Physical Sciences. Nov. 4, 1975. 346(1646): 349-74. Downloaded Apr. 4, 2013. doi: 10.1098/rspa.1975.0180.

Byers et al., Drop Formation from an Orifice in an Electric Field. American Institute of Chemical Engineers. 1988. 34(9): 1577-80.

Deitzel et al., The effect of processing variables on morphology of electrospun nanofibers and textiles. Polymer. 2001. 42: 261-72.

Doshi et al. Electrospinning Process and Applications of Electrospun Fibers. Journal of Electrostatics. 1995. 35:151-60.

Dosunmu et al., Electrospinning of polymer nanofibres from multiple jets on a porous tubular surface. Nanotechnology. Feb. 2, 2006. 17: 1123-7.

Drelich et al., Measurement of interfacial tension in fluid-fluid systems. Encyclopedia of Surface and Colloid Science. 2002. 3152-66.

Feng, The stretching of an electrified non-Newtonian jet: A model for electrospinning. Physics of Fluids. Sep. 23, 2002. 14(11):3912-26. doi: 10.1063/1.1510664.

Forward et al., Free surface electrospinning from a wire electrode. Chemical Engineering Journal. 2012. 183: 492-503. doi:10.1016/j.cej.2011.12.045.

Fromm, Numerical Calculation of the Fluid Dynamics of Drop-on-Demand Jets. IBM Journal of Research and Development. 1984. 28: 322-33.

Gu et al., Process optimization and empirical modeling for electrospun polyacrylonitrile (PAN) nanofiber precursor of carbon nanofibers. European Polymer Journal. Jul. 5, 2005. 41(11). 2559-2568. doi: http://dx.doi.org/10.1016/j.eurpolymj.2005.05.008.

He et al., Scaling law in electrospinning: relationship between electric current and solution flow rate. Polymer. Jan. 10, 2005. 46(8): 2799-2801. doi: http://dx.doi.org/10.1016/j.polymer.2005.01.065.

He et al., The Effect of Electric Field on Droplet Formation and Motion ina Viscous Liquid. The Canadian Journal of Chemical Engineering. Oct. 1991. 69: 1174-83.

Hong, The Dielectric Strength of Air G. Elert (Ed.). The Physics Fact Book. Retrieved from http://hypertextbook.com/facts/2000/AliceHong.shtml. 2000. 3pgs.

Jaworek, Micro- and nanoparticle production by electrospraying. Powder Technology. Feb. 20, 2007. 176: 18-35.

Katta et al., Continuous Electrospinning of Aligned Polymer Nanofibers onto a Wire Drum Collector. Nano Letters. 2004. 4(11):2215-8.

Kim et al., Stability analysis for multi jets electrospinning process modified with a cylindrical electrode. European Polymer Journal. 2006. 42: 2031-8.

Knowles, Dielectric Constant of Ethyl Alcohol Vapor and Possible Effect of Conductivity. The Journal of Physical Chemistry. 1931. 36(10): 2554-66. doi: 10.1021/j150340a003.

Lee et al., Study on droplet formation with surface tension for electrohydrodynamic inkjet nozzle. Journal of Mechanical Science and Technology. 2012. 26(5): 1403-8. DOI 10.1007/s12206-0120301-y.

Liou et al., Three-Dimensional Simulations of the Droplet Formation During the Inkjet Printing process. International Communications in Heat and Mass Transfer. Aug. 22, 2002. 29(8): 1109-18.

Liu et al., One-step electrospun nanofiber-based composite ropes. Applied Physics Letters. 2007. 90: 083108-1-083108-3. Accessed Oct. 13, 2012. doi: 10.1063/1.2644379.

Lu et al., Superhigh-Throughput Needleless Electrospinning Using a Rotary Cone as Spinneret. Small. 2010. 6(15): 1612-6. DOI: 10.1002/smll.201000454.

Pawlowski et al., Electrospinning of a micro-air vehicle wing skin. Polymer. 2003. 44: 1309-14.

Ramakrishnan et al., Studies on preparation of ceramic inks and simulation of drop formation and spread in direct ceramic inkjet printing. Journal of Materials Processing Technology. 2005. 169: 372-81. doi:10.1016/j.jmatprotec.2005.03.021.

Rayleigh, Lord Rayleigh on Equilibrium of Liquid: On the equilibrium of liquid conducting masses charged with electricity. Proc. Roy. Soc. Philosophical Magazine Series 5. May 5, 1881. 14(87):184-6. doi: 10.1080/14786448208628425.

Reneker et al., Nanometre diameter fibers of polymer, produced by electrospinning. Nanotechnology. 1996. 7: 216-23.

Subbiah et al., Electrospinning of Nanofibers. Journal of Applied Polymer Science. 2005. 96(2): 557-69.

Taylor, Disintegration of water drops in an electric field. Proceedings of the Royal Society of London. Series A, Mathematical and Physical Sciences, Jul. 28, 1964. 280(1382) :383-97. doi: 10.1098/rspa.1964.0151. Accessed Jan. 6, 2013.

Taylor, Electrically Driven Jets. Proceedings of Royal Society of London. Series A. Mathematical and Physical Sciences. Dec. 2, 1969. 313 (1515): 453-75. doi: 10.1098/rspa.1969.0205.

Theron et al., Multiple jets in electrospinning: experiment and modeling. Polymer. Mar. 5, 2005. 46(9): 2889-99. doi: http://dx.doi.org/10.1016/j.polymer.2005.01.054.

Thompson et al., Effects of parameters on nanofiber diameter determined from electrospinning model. Polymer. Sep. 15, 2007. 48(23): 6913-22. doi: http://dx.doi.org/10.1016/j.polymer.2007.09.017.

Um et al., Electro-Spinning and Electro-Blowing of Hyaluronic Acid. Biomacromolecules. 2004.5(4): 1426-36.

Wang et al., Formation of water-resistant hyaluronic acid nanofibers by blowing-assisted electro-spinning and non-toxic post treatments. Polymer. 2005. 46: 4853-67.

Wijshoff, The dynamics of the piezo inkjet printhead operation. Physics Reports. 2010. 491: 77-177.

Wilburn, The Business Case for Continuous Manufacturing of Pharmaceuticals. (Master of Business Administration, Master of

(56) References Cited

OTHER PUBLICATIONS

Science in Chemical Engineering), Massachusetts Institute of Technology. May 7, 2010. 53 pages. Published no earlier than Jun. 8, 2010.

Yang et al., A Shield Ring Enhanced Equilateral Hexagon Distributed Multi-needle Electrospinning Spinneret. IEEE Transactions on Dielectrics and Electrical Insulation. Oct. 5, 2010. 17(5): 1592-1601.

Yang et al., Droplet formation from a pulsed vibrating micro-nozzle. Journal of Fluids and Structures. Mar. 4, 2008. 24: 576-88.

Invitation to Pay Additional Fees dated Jul. 12, 2016 for PCT/US2016/029960.

International Search Report and Written Opinion dated Nov. 2, 2016 for Application No. PCT/US2016/029960.

International Preliminary Report on Patentability dated Nov. 9, 2017 for Application No. PCT/US2016/029960.

\* cited by examiner

100

120

110

METHODS AND SYSTEMS FOR MANUFACTURING A TABLET

TECHNICAL FIELD

Methods and systems for manufacturing a tablet are generally described.

BACKGROUND

Pharmaceutical manufacturing technology has generally remained unchanged over the last century due to a combination of heavy regulatory oversight and a well-characterized, deeply established batch manufacturing paradigm. The advent of computers and electronic process control has resulted in higher precision and reliability in pharmaceutical manufacturing, but the industry is still relying on relatively inflexible batch powder processing technology with capital equipment costs tied heavily to the desired production batch size. As a result, equipment and plants designed for a large batch pharmaceutical are typically inefficient at and/or potentially incapable of producing smaller batches of less common pharmaceuticals.

Accordingly, improved systems and methods for manufacturing tablets are needed.

SUMMARY

Methods and systems for manufacturing a tablet are generally described. Certain of the methods and systems described herein involve electrodeposition (e.g., electrospinning) of one or more materials used to fabricate a tablet.

In one aspect, systems for manufacturing a tablet are provided. In some embodiments, the system comprises a substrate having a first electric potential; a source configured to contain a fluid, the source having a second electric potential different than the first electric potential; an emitter associated with the source and configured to emit fluid contained within the source toward the substrate; a die comprising a cavity, the die configured to strip material from an exterior surface of the substrate when the die and the substrate are moved relative to each other; and an actuator associated with the substrate and/or the die and configured to move the die and the substrate relative to each other.

In some embodiments, the system comprises a substrate; a source configured to support a fluid, the source facing the substrate; a die comprising a cavity; and an actuator associated with the substrate and/or the die and configured to move the die and the substrate relative to each other.

In another aspect, methods are provided. In some embodiments, the method comprises electrospinning a material on a rotating substrate such that the material accumulates on the substrate while it is rotated, moving a die comprising a cavity and the substrate relative to each other such that at least a portion of the accumulated material is stripped from the substrate into the cavity of the die; and applying a compressive force to the accumulated material within the cavity of the die to form the tablet.

According to certain embodiments, the method comprises electrodepositing a material on a substrate such that the material accumulates on the substrate, and moving a die comprising a cavity and the substrate relative to each other such that at least a portion of the accumulated material is stripped from the substrate into the cavity of the die.

In some embodiments, the method comprises establishing a first electric potential at a source containing a material, and establishing a second electric potential, different than the first electric potential, at a substrate comprising an elongated rod such that the material is electrodeposited on the elongated rod.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
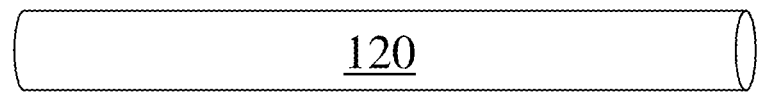
FIGS. 1A-1D are schematic diagrams of a system for manufacturing a tablet including a source and a substrate, according to one set of embodiments.
Figure 1A:
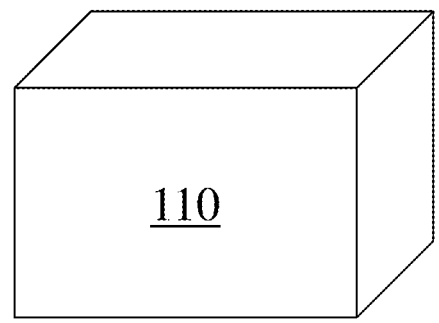

Methods and systems for manufacturing a tablet are generally provided. Certain embodiments comprise electrodepositing (e.g., electrospinning) a material (e.g., the tablet material, for example, within a fluid) onto a substrate. The substrate can be, for example, an elongated rod. In some such embodiments, after material has been electrodeposited onto the substrate, a die comprising a cavity and the substrate can be moved relative to each other such that the electrodeposited material is at least partially stripped from the substrate and/or at least partially deposited into the cavity of the die. Some embodiments comprise compressing the material in the cavity to form a tablet.

Certain of the systems described herein comprise a substrate (e.g., an elongated rod) and a source (e.g., a reservoir) configured to support a fluid (e.g., comprising a tablet material) facing the substrate. In certain embodiments, the source (e.g., the reservoir) and the substrate (e.g., elongated rod) have different electric potentials (e.g., such that the material supported by the source is electrodeposited onto the substrate). Certain systems may also comprise a die comprising a cavity and an actuator. The actuator can be associated with the substrate (e.g., elongated rod) and/or the die and can be configured to move the die and the substrate relative to each other. In this way, according to certain embodiments, the actuator can be used to at least partially remove the electrodeposited material from the substrate into a cavity of the die. Optionally, after the material has been transferred into the cavity of the die, according to certain embodiments, a compressive force may be applied to the material within the die cavity (e.g., using a plunger) such that the compressed material within the die cavity forms a tablet.

Certain of the electrodeposition-based systems described herein can be useful, for example, for small and large scale pharmaceutical and/or food manufacturing applications. In addition, certain of the systems and methods described herein may offer one or more advantages over traditional tableting methods and systems. For example, certain of the systems and methods described herein can reduce (e.g., minimize) user exposure to airborne particulates. Such airborne particulates may, in some cases, comprise particles of active pharmaceutical ingredients (APIs) such as those produced in powder-based pharmaceutical manufacturing processes. Certain of the systems and methods described herein can be used as part of a continuous manufacturing processes (e.g., processes for continuously producing solid tablets from a solution), which might not otherwise be possible using traditional methods and systems. Certain embodiments may also lead to increased tablet production speeds and/or reduced manufacturing costs. In addition, some of the embodiments described herein can be employed while using relatively few moving parts and/or manufacturing steps. In some cases, employing certain of the systems and methods described herein significantly reduces the amount of time needed to dry tablet materials as compared to fluid-based systems which generally require liquid to be evaporated and/or removed which may consume a large portion of the total manufacturing time and/or may significantly increase costs. For example, in some embodiments in which the tablet material is deposited using electrospinning, the production of tablet-material-containing fibers with high surface to volume ratios can allow for the relatively quick removal (e.g., evaporation) of liquid from the deposited material.

Figure 1B:
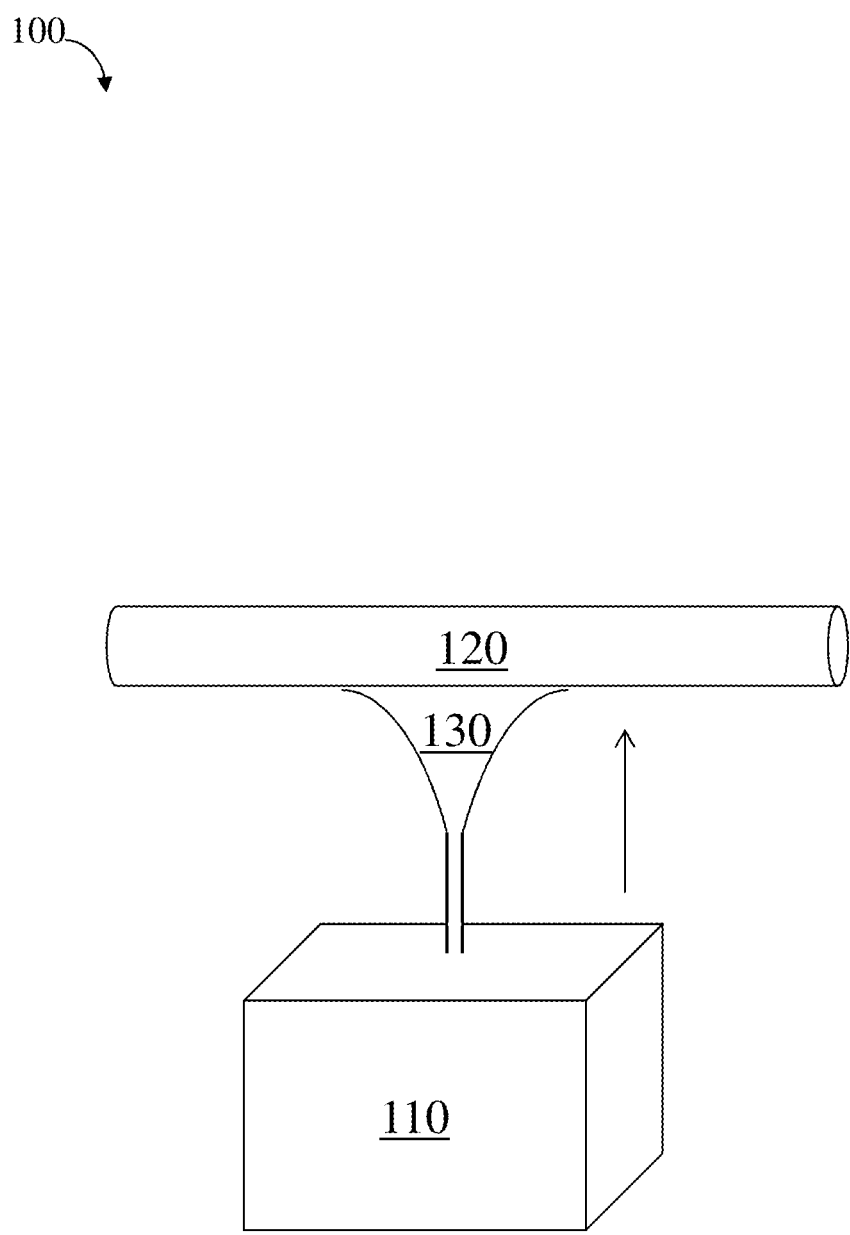

As illustrated in FIG. 1A, system 100 comprises a source 110 (e.g., a reservoir) and a substrate 120 (e.g., an elongated rod). In some embodiments, source 110 is located proximate to substrate 120. For example, in some cases, the substrate is located proximate to the source such that material supported by and/or contained within the source can be transferred to and deposited on at least a portion of the substrate (e.g., by electrodeposition). The source may be configured to contain and/or support a material for electrodeposition. The substrate and the source may be separated by any suitable distance including, but not limited to, distances over which electrodeposition (e.g., electrospinning) can occur. In some embodiments, as illustrated in FIG. 1B, material 130 is transferred (e.g., electrodeposited) from source 110 and deposited on at least a portion of substrate 120, as indicated by the arrow in FIG. 1B. In some embodiments, the source faces the substrate. For example, in some embodiments, the source faces the substrate such that the material supported on and/or contained within the source has at least a surface facing the substrate. In some embodiments, the system is configured such that the material accumulates on the substrate after it has been electrodeposited.

Figure 1C:
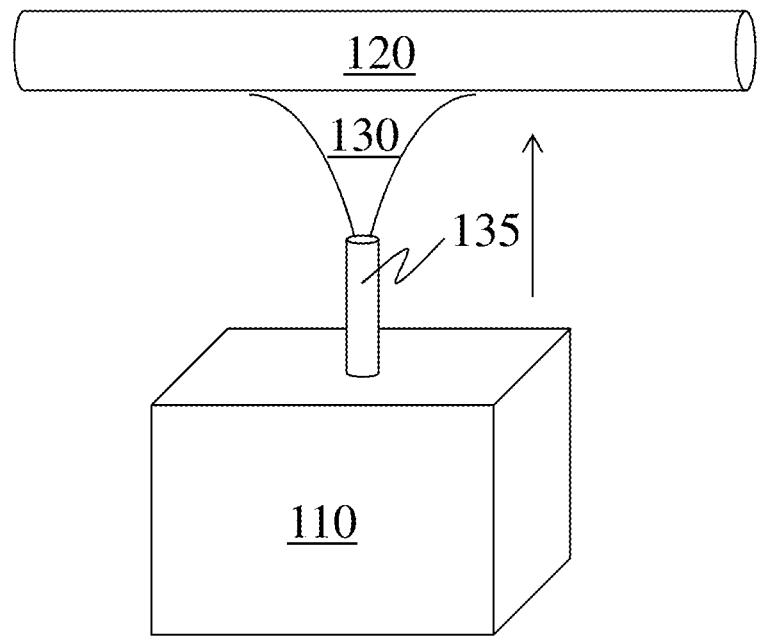

In some cases, the source comprises an emitter. In certain embodiments, the emitter is configured to transfer the material from the source to the substrate (e.g., during electrodeposition). As illustrated in FIG. 1C, in some embodiments, source 110 comprises emitter 135, such that material 130 is transferred from source 110 to substrate 120 via emitter 135. In certain embodiments, the emitter is an outlet of the source (e.g., a nozzle). In some embodiments, the source comprises a single emitter or a plurality of emitters. For example, in certain embodiments, the source comprises one or more, two or more, three or more, or four or more emitters.

In some embodiments, material from the source is deposited on the substrate. In some embodiments, the material is electrodeposited onto the substrate. Electrodeposition may include, for example, electro-spinning and electrospraying. For example, in some embodiments, the electrodeposition can comprise electrospinning such that one or more elongated threads or fibers are formed between the source and the substrate. In some embodiments, the electrodeposition can comprise electrospraying such that particles and/or droplets are deposited from the source onto the substrate.

In an exemplary electrodeposition process, one or more materials (e.g., one or more active pharmaceutical ingredient(s) (along with any optional desired excipients)) may be mixed with a fluid containing the one or more materials. In some cases, the fluid may comprise a polymer that aids in the electrodeposition of the material. In some embodiments, a carrier liquid may be used to dissolve and/or suspend the material. In some embodiments, the carrier liquid can be highly volatile (e.g., having a boiling point less than about 100° C.). Carrier liquids are described in more detail, below. Because of the high surface area generated during electrodeposition, the evaporation rate of the carrier liquid can be high, according to certain embodiments, allowing for more efficient drying at ambient temperatures than might be observed with other tablet preparation techniques such as thin film casting. In addition, in some embodiments, no heat is necessary to blend ingredients during electrodeposition, as they may already be well blended in the solution prior to electrodeposition. In some embodiments, electrodeposition is more suitable for downstream processing of heat-sensitive materials (e.g., heat-sensitive APIs) than other preparation techniques, e.g., melt extrusion.

In certain embodiments, the system is configured such that the substrate and the source have different electric potentials. In some embodiments, the substrate has a first electric potential and the source has a second electric potential different than the first electric potential. For example, a first electric potential can be established at the source (e.g., the reservoir) containing and/or supporting the material and a second electric potential, different from the first electric potential, can be established at the substrate (e.g., the elongated rod) such that the material is electrodeposited on the substrate. In some embodiments, the first electric potential is less than the second electric potential. In certain embodiments, the first electric potential is greater than the second electric potential.

Figure 1D:
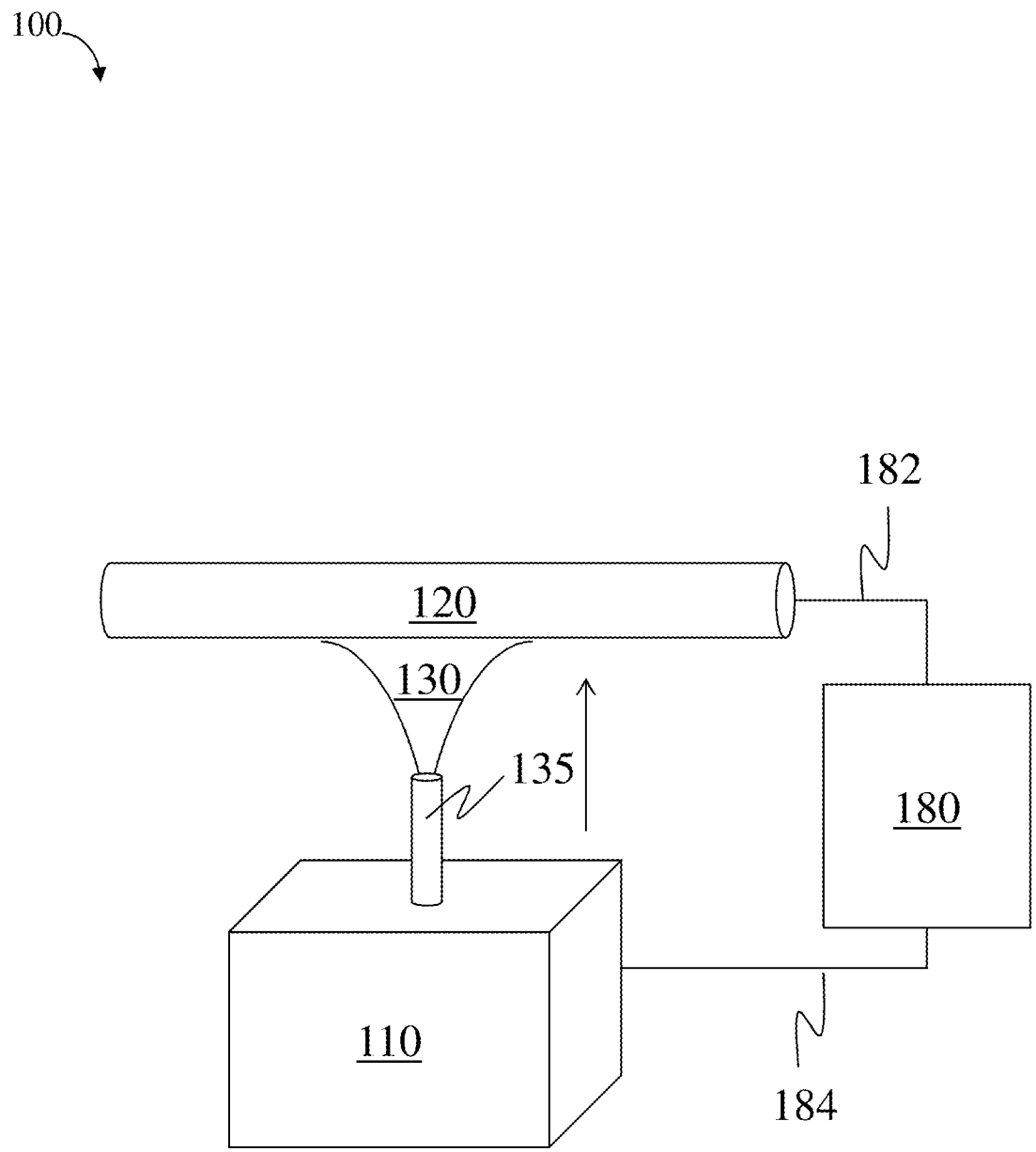

The system may comprise, in some embodiments, an electric potential generator electrically connected to the substrate and/or the source. In some embodiments, the electric potential generator generates the first and/or second electric potentials. For example, as illustrated in FIG. 1D, system 100 may comprise electric potential generator 180 electrically connected to substrate 120 and source 110 via electrical connectors (e.g., electrical leads such as wires) 182 and 184. Those skilled in the art would be capable of selecting suitable electric potential generators and electrical connections for use with the systems and methods described herein.

In certain embodiments, the substrate is not electrically connected to the source. For example, in some embodiments, the source is connected to the electric potential generator and the substrate is electrically connected to an electrical ground. In certain embodiments, the source is connected to the electrical ground and the substrate is connected to the electric potential generator. In some embodiments the substrate and/or the source has an electric potential of at least about 10 kV. In certain embodiments, the substrate and/or the source has an electric potential of at least about 10 kV, at least about 20 kV, at least about 40 kV, at least about 50 kV, at least about 70 kV, or at least about 90 kV. In some embodiments, the substrate and/or the source has an electric potential of less than or equal to about 100 kV, less than or equal to about 90 kV, less than or equal to about 70 kV, less than or equal to about 50 kV, less than or equal to about 40 kV, or less than or equal to about 20 kV. Combinations of the above referenced ranges are also possible (e.g., between about 10 kV and about 100 kV). Other ranges are also possible.

In some embodiments, the electric potential generator generates an electric field. In certain embodiments, the electric field has an electric field strength of at least about 0.1 kV/cm, at least about 0.5 kV/cm, at least about 1 kV/cm, at least about 2 kV/cm, or at least about 5 kV/cm. In some embodiments, the electric field has an electric field strength of less than or equal to about 10 kV/cm, less than or equal to about 5 kV/cm, less than or equal to about 2 kV/cm, less than or equal to about 1 kV/cm, or less than or equal to about 0.5 kV/cm. Combinations of the above referenced ranges are also possible (e.g., between about 0.1 kV/cm and about 10 kV/cm). Other ranges are also possible.

Figure 1E:
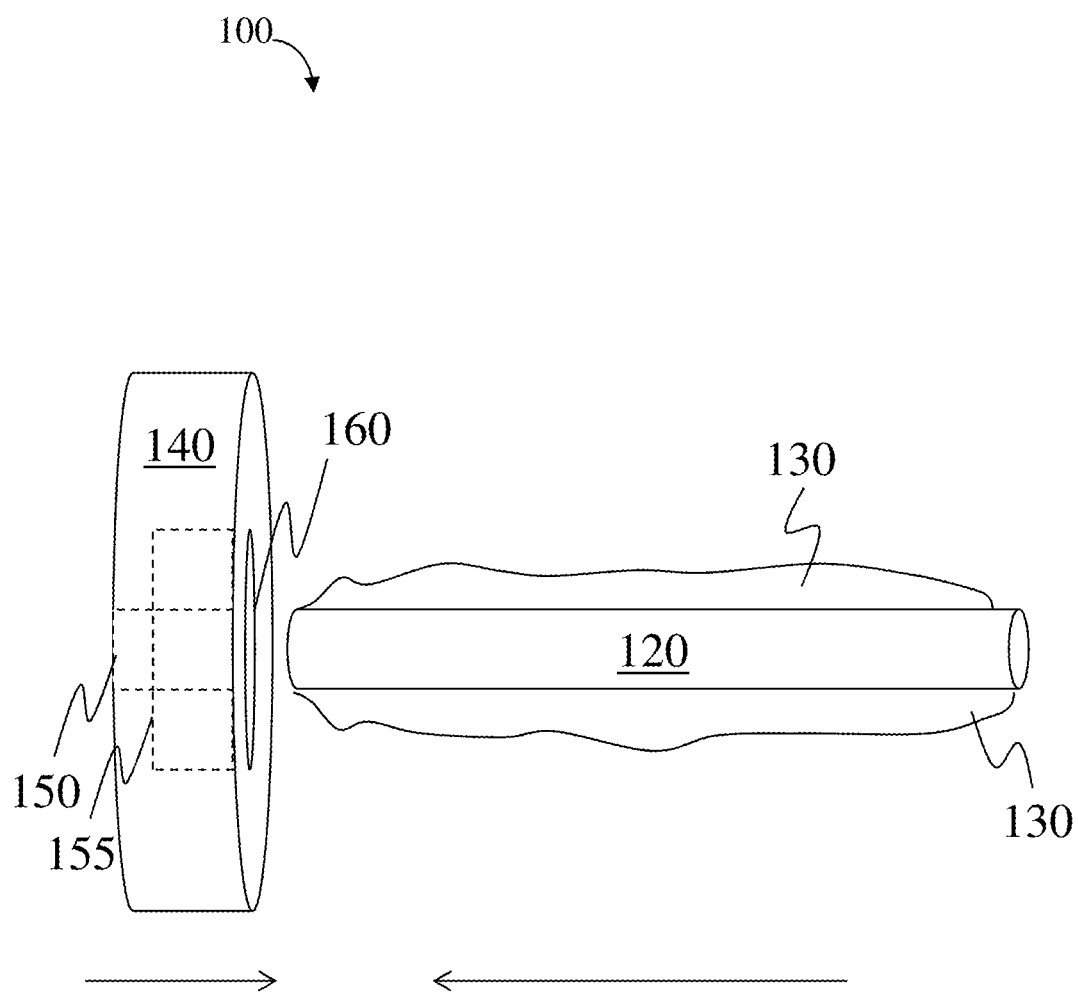
FIGS. 1E-1G are schematic diagrams of a system for manufacturing a tablet including a die, according to one set of embodiments.
Figure 1F:
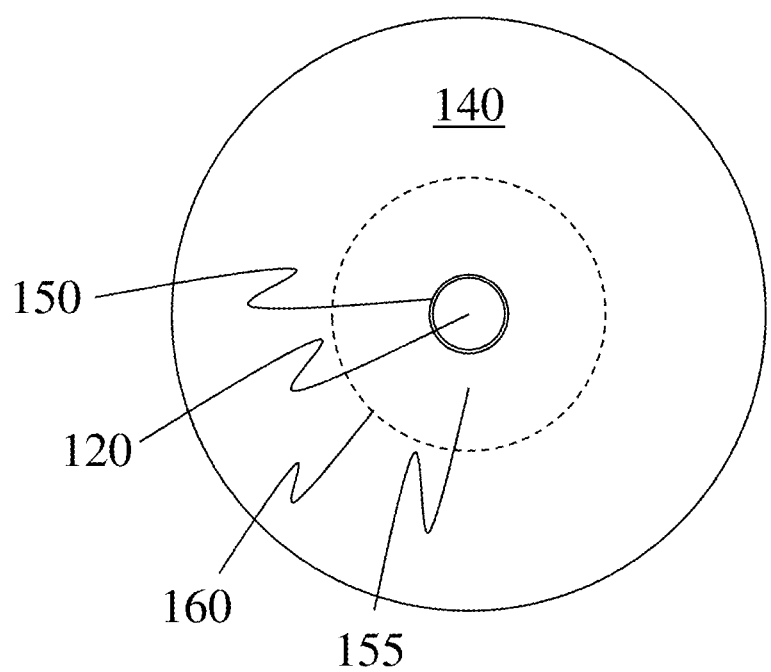

In some embodiments, at least a portion of the material (e.g., the electrodeposited material) is removed from the substrate. In certain embodiments, material is removed from the substrate using a die. In some embodiments, the die used to remove electrodeposited material comprises a cavity. For example, as illustrated in FIG. 1E system 100 comprises source 110, substrate 120 located proximate source 110, material 130 associated with at least a portion of an exposed surface of the substrate 120, and die 140. In some such embodiments, die 140 comprises an opening 150 and a cavity 160. The opening may be configured, in certain embodiments, to circumscribe the substrate. For example, in FIG. 1E, opening 150 is configured to circumscribe substrate 120. In some embodiments, the opening of the die has a shape and/or size such that at least a portion of the substrate may enter into and pass through the opening. For example, as illustrated in FIG. 1F, in some embodiments, opening 150 of die 140 has a shape and/or size such that at least a portion of substrate 120 may enter into and pass through opening 150. In certain embodiments, the opening has a cross-section mated with a cross-section of the substrate. In FIG. 1F, for example, opening 150 has a cross-section that is mated with the cross-section of substrate 120. In some embodiments, a cross-sectional shape of the opening may be substantially similar to a cross-sectional shape of the substrate. In some cases, a cross-sectional dimension of the opening may be about equal to (e.g., within about 5% of) a cross-sectional dimension of the substrate, such that the substrate may pass through the opening. For example, referring again to FIG. 1F, the cross-sectional diameter of opening 150 may be about equal to the cross-sectional diameter of substrate 120.

According to certain embodiments, the die can be configured to remove at least a portion of the material from an exterior surface portion of the substrate. For example, in some embodiments, when the die and the substrate are moved relative to each other, at least a portion of the material (e.g., material 130 in FIG. 1E) can be removed from an exterior surface portion of the substrate. In certain embodiments, at least a portion of the material associated with at least a surface of the substrate is removed from the substrate as the substrate passes through the opening and/or the cavity of the die. In some embodiments, at least a portion of the removed material may be disposed within the cavity of the die. For example, in some embodiments, at least a portion of the material is stripped from the substrate and transferred into the cavity of the die.

In some embodiments, a least a portion of the material that has been electrodeposited on at least a portion of an exterior surface of the substrate is removed from the surface portion by moving the substrate and die relative to each other such that at least a portion of the substrate passes through the cavity and the opening of the die. In some such embodiments, the die and the deposited material interact such that the material is dissociated from the exterior surface portion of the substrate. The die can remove material from the exterior surface of the substrate, for example, by scraping the material from the substrate. In some such embodiments, the removed material can be collected in the cavity as the substrate passes through the die. For example, in some embodiments, the material is at least partially removed from the substrate as the substrate passes through the opening, depositing the portion of removed material in the cavity.

Figure 1G:
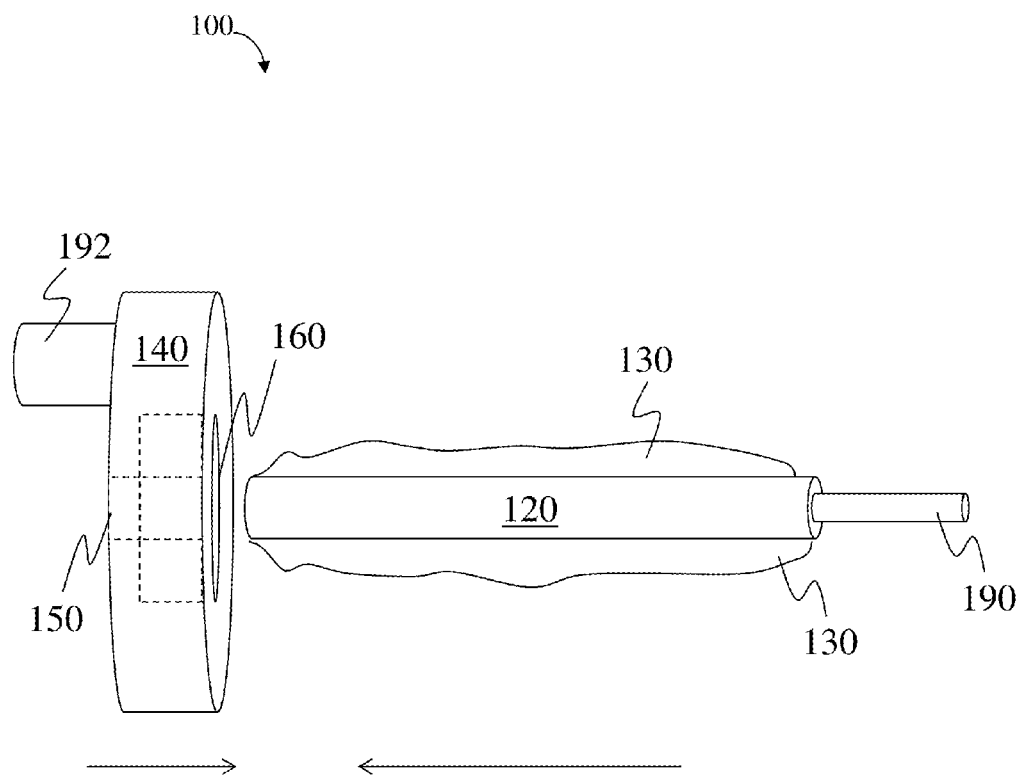

For example, in an exemplary embodiment, and illustrated in FIGS. 1E and 1G substrate 120 can be an elongated rod, and the elongated rod and die 140 can be moved relative to each other such that material 130 is scraped from the external surface of the substrate into the cavity of the die via the interaction of surface 155 of die 140 and material 130 as the elongated rod passes through opening 150 of die 140.

In certain embodiments, the die and the substrate are moved relative to each other such that the material is disassociated from the surface of the substrate. Referring again to FIG. 1E, die 140 and substrate 120 may move relative to each other as indicated by the arrows. For example, in some embodiments, substrate 120 is moved towards and through die 140 while die 140 is held stationary. In certain embodiments, die 140 is moved towards substrate 120 such that substrate 120 passes through opening 150, while substrate 120 is held stationary. In some cases, both die 140 and substrate 120 are moved, resulting in movement relative to each other.

As noted above, in some embodiments, the die and the substrate can be moved relative to each other using an actuator. In some embodiments, the actuator comprises a linear actuator. The actuator is configured, according to certain embodiments, to move the die and the substrate relative to each other. In some embodiments, the actuator is associated with the die, and the actuator is configured to move the die. In certain embodiments, the actuator is associated with the substrate, and the actuator is configured to move the substrate. According to some embodiments, the actuator is associated with the substrate and the die, and the actuator is configured to move both the substrate and the die. For example, as illustrated in FIG. 1G, system 100 comprises an actuator 190 associated with the substrate and/or an actuator 192 associated with the die, wherein actuator 190 and/or 192 is configured to move the die and the substrate relative to each other, as indicated by the arrows in FIG. 1G. Actuators such as linear actuators are known in the art and those skilled in the art would be capable of selecting a suitable actuator for use with the systems and methods described herein. Non-limiting examples of suitable linear actuators include electric linear actuators, threaded linear actuators, hydraulic actuators, pneumatic actuators, piezoelectric actuators, electro-mechanical actuators, telescoping actuators, or the like.

Figure 1H:
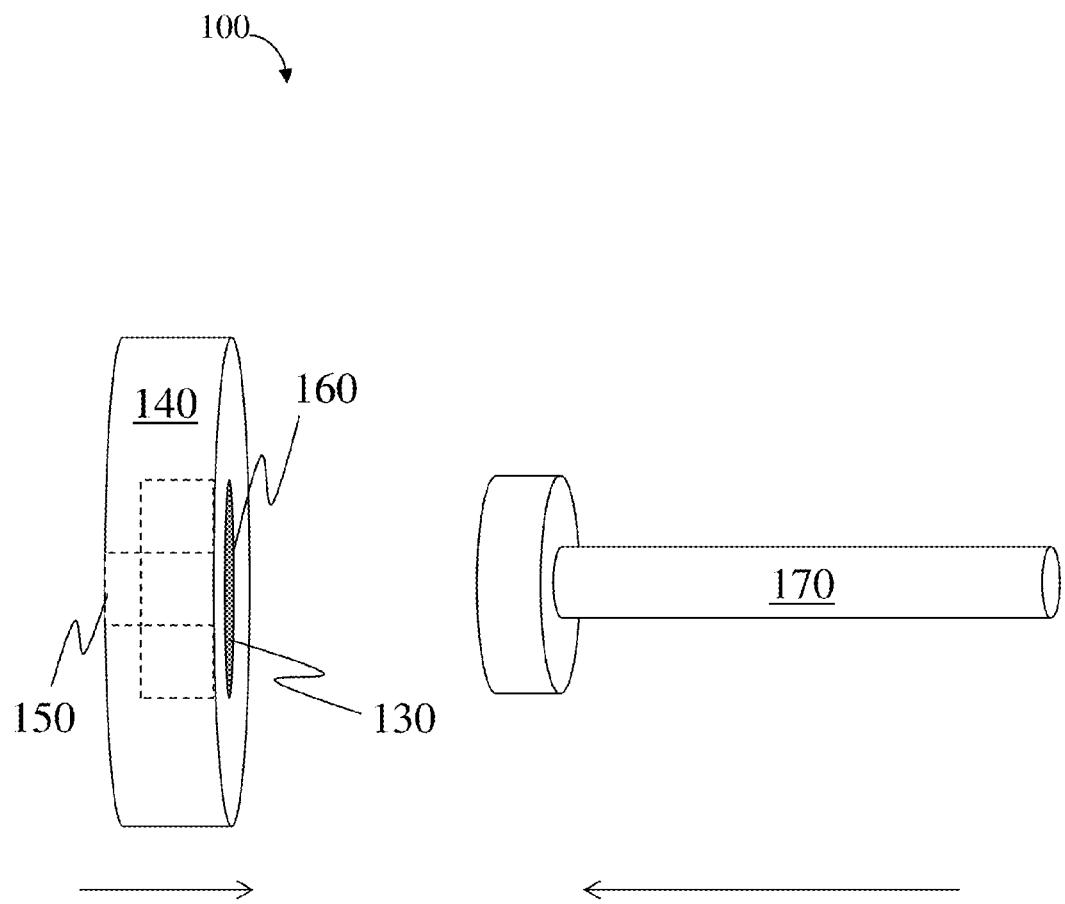
FIG. 1H is a schematic diagram of a system for manufacturing a tablet including a compaction plunger, according to one set of embodiments.

In some embodiments, a compressive force may be applied to the material contained within the cavity. In certain embodiments, the compressive force is applied to the material to form a tablet comprising the material. In certain embodiments, the system comprises a plunger configured to apply the compressive force to the material contained within the cavity. For example, as illustrated in FIG. 1H, system 100 comprises die 140 comprising opening 150 and cavity 160, material 130 contained within at least a portion of cavity 160, and a plunger 170. In some embodiments, plunger 170 is a compaction plunger. Plunger 170, in certain embodiments, is configured to be aligned with and/or mated with cavity 160 such that the material contained within the cavity may be compressed. In some embodiments, a second actuator is associated with the plunger and/or the die and is configured to move the plunger and the die relative to each other, as indicated by the arrows in FIG. 1H. For example, in some such embodiments, the second actuator is configured to the move the plunger and the die relative to each other such that the material within the cavity is compacted.

Figure 2:
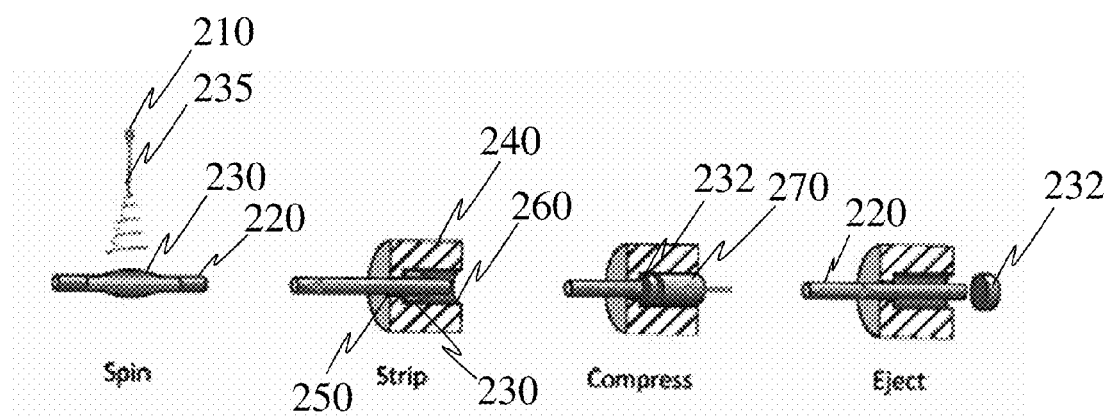
FIG. 2 is a schematic diagram of a method for manufacturing a tablet, according to one set of embodiments.

The systems and methods described herein are useful for, in some embodiments, the formation of a tablet. Tablets, for example, may contain API and/or an ingestible composition mixed with a solid excipient and/or other additives as needed to achieve the desired size, strength, friability, dissolution rate, and the like. In some cases, the tablet is manufactured by compressing the material deposited within the cavity and ejecting the formed tablet from the cavity. FIG. 2 is a schematic illustration of a process, according to certain embodiments, in which material is electrodeposited onto a substrate, removed from the substrate, and compacted to form a tablet. In an exemplary embodiment, as illustrated in FIG. 2, the methods comprise transferring material 230 from source 210 to substrate 220 via electrodeposition from emitter 235 to substrate 220. In some embodiments, an electrical potential may be applied to the source and/or the substrate, such that the material (and/or liquid) contained within and/or supported by the source may be expelled from the emitter toward the substrate. For example, in FIG. 2, the potential may be applied to source 210 which results in movement of the liquid to emitter 235. Then, in certain embodiments, liquid is emitted from emitter 235 in the direction of substrate 220, onto which the liquid is deposited. In some embodiments, the liquid is dried, forming a solid electrodeposited material on the substrate. In certain embodiments, the source does not contain a liquid and the electrodeposited material is deposited in dry form. At least a portion of electrodeposited material 230 may then be removed (e.g., stripped) from substrate 220 by passing substrate 220 through die 240 comprising opening 250 and cavity 260. As substrate 220 is passed through opening 250, at least a portion of the surface of cavity 260 scrapes at least a portion of material 230 from substrate 220, depositing material 230 in cavity 260. In some embodiments, plunger 270 may be used to apply a compressive force to material 230 deposited in cavity 260 to form tablet 232 comprising the material. Tablet 232 may be removed (e.g., ejected) from die 240 by, for example, passing substrate 220 through opening 250 such that tablet 232 is ejected.

Figure 3A:
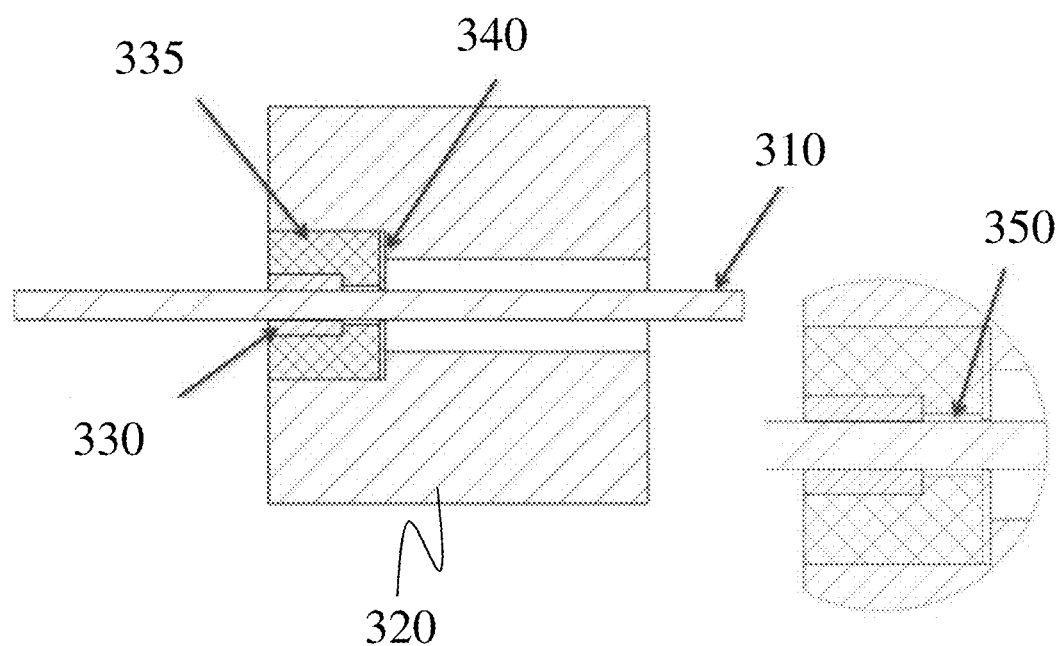
FIG. 3A is a schematic diagram of a system for manufacturing a tablet, according to one set of embodiments.
Figure 3B:
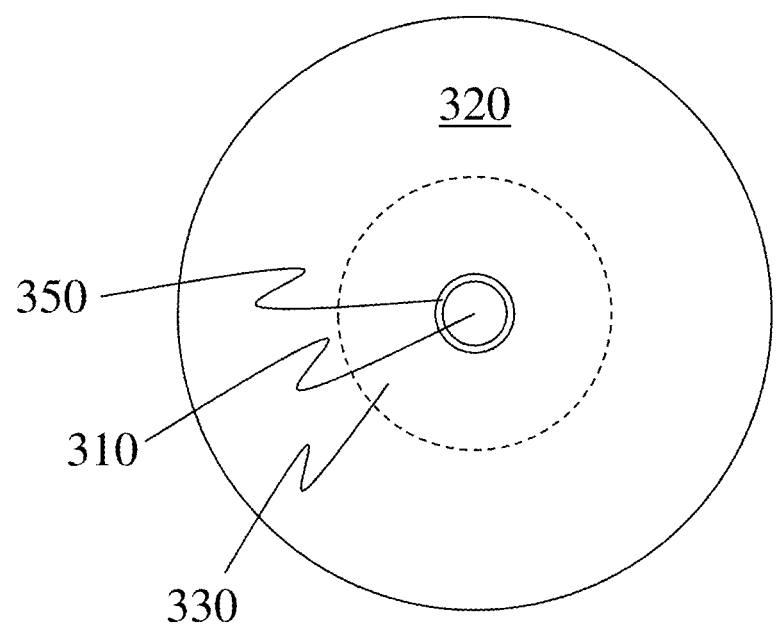
FIG. 3B is a cross-sectional view of the system in FIG. 3A, according to one set of embodiments.

As described above, in some embodiments, at least a portion of the electrodeposited material is disassociated from at least a portion of the exterior surface of the substrate by moving the substrate and the die relative to each other. In some such embodiments, moving the substrate and the die relative to each other comprises passing at least a portion of the substrate through the cavity of the die. An exemplary embodiment is illustrated in FIG. 3A, in which substrate 310 (e.g., a rod) and die 320 are moved relative to each other such that substrate 310 passes through die 320. (FIG. 3B is a cross-sectional view of the system of FIG. 3A.) In some embodiments, the die comprises a cavity and an opening. For example, in FIG. 3A, die 320 comprises cavity 330 (defined by cavity wall 335) and opening 350. In some embodiments, the cavity comprises a stripping wall. For example, in FIG. 3A, cavity 330 comprises a stripping wall 340. In certain embodiments, the stripping wall facilitates removal of electrodeposited material from the substrate, facilitates the deposition/collection of the material in the cavity, and/or inhibits and/or prevents the material from passing through the opening. For example, in FIG. 3A, stripping wall 340 facilitates removal of electrodeposited material from substrate 310, facilitates the deposition/collection of electrodeposited material in cavity 330, and prevents electrodeposited material from passing through opening 350.

The substrate may comprise any suitable material for electrodeposition. In some embodiments, the substrate comprises a conductive material. In certain embodiments, the substrate comprises a metal (e.g., steel, aluminum, brass, copper). In some embodiments, the substrate comprises a polymer (e.g., polyethylene, polypropylene, polyethylene terephthalate, and/or composites of these.). In certain embodiments, the polymer is a conductive polymer. In some cases, the substrate may comprise a ceramic. In certain embodiments, the substrate comprises glass. In some cases, the substrate comprises a conductive coating (e.g., a polymer substrate coated with a metal coating). In some embodiments, the substrate is a paper-like substrate such as wax paper, parchment paper, or the like. In some such embodiments, the paper-like substrate may be adjacent a second substrate comprising a conductive material such as metal (e.g., metal wire, metal plate) such that the second substrate has an electric potential different than the electric potential of the source and/or emitter.

In some embodiments, the substrate is a rod. In certain embodiments, the substrate is an elongated rod. The elongated rod can have a length dimension and a longitudinal axis extending substantially parallel to its length dimension. The rod can also have a cross-sectional dimension substantially perpendicular to the length dimension. The cross-sectional dimension of the rod at a particular location on the rod corresponds to the maximum cross-sectional distance extending through the geometric center of the cross-section of the rod and spanning opposed boundaries of the cross-section of the rod. In cases in which the cross-sectional shape of the rod varies along the longitudinal axis of the rod, the cross-sectional dimension of the rod is the numerical average of the cross-sectional dimensions at each point along the longitudinal axis of the rod.

In some embodiments, the elongated rod has an aspect ratio (i.e., the ratio of the length dimension of the rod to the cross-sectional dimension of the rod, expressed as length: cross-sectional dimension) of at least about 3:1, at least about 5:1, at least about 10:1, at least about 20:1, or at least about 50:1.

In certain embodiments, the elongated rod has a first coordinate direction corresponding to the longitudinal axis of the elongated rod. In some such embodiments, the elongated rod has a second coordinate direction orthogonal to the first coordinate direction and a third coordinate direction orthogonal to the first and second coordinate directions. In some embodiments, the ratio of the length of the elongated rod along the first coordinate direction (i.e., the length of the longitudinal axis of the elongated rod) to the length of the elongated rod along the second coordinate direction is at least about 3:1, at least about 5:1, at least about 10:1, at least about 20:1, or at least about 50:1. In some embodiments, the ratio of the length of the elongated rod along the first coordinate direction to the length of the elongated rod along the third coordinate direction is at least about 3:1, at least about 5:1, at least about 10:1, at least about 20:1, or at least about 50:1.

In certain embodiments, the substrate has an exterior surface comprising protrusions. The protrusions, in some cases, may assist deposition and/or removal of the material on the substrate. In certain embodiments, the substrate may comprise features (e.g., a roughened surface) such that the protrusions comprise the features. In some embodiments, the substrate may be threaded. For example, in some embodiments, the protrusions may be part of a threaded external surface of the substrate. Those of ordinary skill in the art are familiar with threaded surfaces, in which a plurality of protrusions extend substantially parallel across the external surface of the substrate. In some embodiments, the protrusions form a substantially helical shape across the external surface of the substrate.

In some embodiments, the substrate may be rotated. For example, in some embodiments, the material is electrodeposited on a rotating substrate such that the material accumulates on the substrate while it is rotated. In some such embodiments, an actuator is associated with the substrate and may rotate the substrate. For example, referring again to FIG. 1G, actuator 190 may be a rotary actuator. In some embodiments, an actuator associated with the substrate may be of two or more different types. For example, in some embodiments, an actuator associated with the substrate may be both a linear actuator and a rotary actuator. That is to say, the actuator may be capable of both rotating the substrate and moving the substrate in a substantially linear direction. In FIG. 1G, for example, actuator 190 may comprise a rotary actuator and a linear actuator. Rotary actuators are known in the art and those skilled in the art would be capable of selecting suitable rotary actuators for use with the systems and methods described herein. Non-limiting examples of suitable rotary actuators include electric rotary actuators and fluid rotary actuators. In certain embodiments, the substrate is rotated during removal of the material from the substrate. For example, in some embodiments, the substrate is rotated when the die and the substrate are moved relative to each other, such that the deposited material is disassociated from the substrate. In some embodiments, the substrate may be rotated at a rate of at least about 1 revolution per minute (RPM), at least about 5 RPM, at least about 10 RPM, and/or at least about 100 RPM (and/or, in some embodiments, up to about 1000 RPM, up to about 10,000 RPM, or more). Rates of rotation outside these ranges are also possible, in some embodiments.

As noted above, in some embodiments, the electrodeposited material can originate from a source. The source can be configured, according to certain embodiments, to support and/or contain the material that is to be electrodeposited. In some embodiments, the source is configured to support and/or contain a fluid comprising the material that is to be electrodeposited. In some embodiments, the source is a reservoir. In certain embodiments, the source is a fluid container such as a tank, a bottle, a tube, a tub, or the like. The reservoir can have any of a variety of suitable sizes. In some embodiments, the reservoir has a size of at least about 1 cm$^3$, at least about 10 cm$^3$, at least about 100 cm$^3$, or at least about 1000 cm$^3$ (and/or, in some embodiments, up to about 10 liters, up to about 100 liters, up to about 1000 liters, or more). The reservoir can also have any of the variety of suitable shapes.

The source may also comprise any suitable material. Non-limiting examples of suitable source materials include, but are not limited to, metals, polymers, and the like. In some embodiments, the source comprises an electrically conductive material.

In certain embodiments in which the source supports and/or contains a fluid comprising the material to be deposited, the source comprises a pathway to apply an electrical potential to the fluid. The pathway to apply an electrical potential to the fluid may comprise the source itself, in some embodiments. For example, in some embodiments, the source comprises an electrically conductive material such that the electrical potential generated by the electric potential generator electrically connected to the source is applied to the fluid. In some embodiments, the source comprises a separate electrically conductive pathway between the electrical potential generator and the fluid, such as an electrical wire between the fluid and the electric potential generator.

In certain embodiments, the source comprises a mixer. For example, in some embodiments, the source comprises a mixing rod such that the material is transferred to the substrate at a faster rate as compared to transferring the material without a mixing rod. In certain embodiments, the mixing rod maintains a relatively homogeneous mixture of the material in solution. Non-limiting examples of suitable mixers include magnetic stir bars, propellers, augers, or any other suitable mixers. The choice of mixer may depend on such factors as, for example, the type of material being deposited, and/or the viscosity of the fluid being deposited.

In some embodiments, the system comprises a emitter associated with the source. In an exemplary embodiment, the system comprises an emitter associated with the source configured to emit the material or a fluid comprising the material such that the material is deposited on the substrate (e.g., elongated rod). In certain embodiments, the emitter is a dispenser. In some embodiments, the emitter may be auger shaped. For example, the emitter may comprises an auger shaped rod disposed within the source such that material is brought closer to the substrate when the emitter is rotated within the source. In some embodiments, the emitter is a feature from which the material to be deposited is released. For example, in certain embodiments, the emitter comprises a needle, a nozzle, a valve, a tube, an orifice, or the like. In some embodiments, the emitter comprises a porous material through which the material may flow. In certain embodiments, the emitter comprises a surface that imparts curvature (e.g., such as in the form of a droplet) to the surface of the material or fluid to be emitted from the emitter to the substrate. For example, in some such embodiments, the emitter comprises a wire, a rod, a screw, a roller, bubbles, or the like, such that the surface of the material or fluid on at least a surface of the emitter is curved.

The emitter may comprise any suitable material for electrodeposition. In some embodiments, the emitter comprises a conductive material. In certain embodiments, the emitter comprises a metal (e.g., steel, aluminum, brass, copper). In some embodiments, the emitter comprises a polymer (e.g., polyethylene, polypropylene, polyethylene terephthalate, and/or composites of these). In certain embodiments, the polymer is a conductive polymer. In some cases, the emitter may comprise a ceramic. In certain embodiments, the emitter comprises glass (e.g., a glass tube such as a glass pipette). In some cases, the emitter comprises a conductive coating (e.g., a polymer substrate coated with a metal coating). In certain embodiments, the emitter has an exterior surface comprising protrusions. The protrusions, in some cases, may assist deposition of the material on the substrate. In certain embodiments, the emitter may comprise features (e.g., a roughened surface) such that the protrusions comprise the features. In some embodiments, the emitter may be threaded. For example, in some embodiments, the protrusions may be part of a threaded external surface of the emitter. Those of ordinary skill in the art are familiar with threaded surfaces, in which a plurality of protrusions extend substantially parallel across the external surface of the emitter. In some embodiments, the protrusions form a substantially helical shape across the external surface of the emitter.

A surface of the source closest to the substrate, or an end of the emitter facing the substrate, may be separated from the substrate by a particular separation distance such that, for example, efficient transfer of the material occurs. In some cases, the electric potential applied to the substrate and/or the source such that electrodeposition occurs may be reduced by decreasing the separation distance. In some embodiments, the separation distance between the surface of the emitter (or surface of the source) closest to the substrate and the substrate may be between about 100 mm and about 500 mm. In certain embodiments, the separation distance is at least about 100 mm, at least about 150 mm, at least about 200 mm, at least about 300 mm, or at least about 400 mm. In some embodiments, the separation distance is less than or equal to about 500 mm, less than or equal to about 400 mm, less than or equal to about 300 mm, less than or equal to about 200 mm, or less than or equal to about 150 mm. Combinations of the above referenced ranges are also possible (e.g., between about 100 mm and about 500 mm, between about 150 mm and about 300 mm). Other ranges are also possible. Those skilled in the art would be capable of selecting suitable separation distances based upon the teachings of this specification.

Material may be deposited onto the substrate at a variety of suitable flow rates. For example, in some embodiments, the flow rate of the material (and/or the fluid comprising the material) from the source to the substrate may be between about 0.001 mL/min and about 10 mL/min. In some embodiments, the flow rate of the material from the source to the substrate may be at least about 0.001 mL/min, at least about 0.005 mL/min, at least about 0.01 mL/min, at least about 0.05 mL/min, at least about 0.1 mL/min, at least about 0.5 mL/min, at least about 1 mL/min, or at least about 5 mL/min. In certain embodiments, the flow rate of the material from the source to the substrate is less than or equal to about 10 mL/min, less than or equal to about 5 mL/min, less than or equal to about 1 mL/min, less than or equal to about 0.5 mL/min, less than or equal to about 0.1 mL/min, less than or equal to about 0.05 mL/min, less than or equal to about 0.01 mL/min, or less than or equal to about 0.005 mL/min. Combinations of the above referenced ranges are also possible (e.g., between about 0.001 mL/min and about 10 mL/min). Other ranges are also possible. Those skilled in the art would be capable of selecting suitable flow rates depending on the size of the emitter, the solutions and/or materials used, and/or temperature of the electrodeposition, based on the teachings of this specification.

In some embodiments, the material is deposited onto the substrate under ambient conditions such as atmospheric pressure and/or room temperature (e.g., between about 20° C. and about 25° C.). Other pressures and/or temperatures are also possible. Those skilled in the art would be capable of selecting suitable temperatures and pressures for depositing the material depending on the solutions and/or materials used, based on the teachings of this specification.

As noted above, in some embodiments, the die comprises a cavity. The cavity may comprise any suitable shape. For example, in some embodiments, the cavity occupies a volume such that the volume of the finally-formed tablet is defined by the cavity. For example, the tablet may have the same size/shape as the cavity after compaction of the material.

The cavity can have any of a variety of suitable cross-sectional shapes. The cross-section of the cavity generally refers to the cross-section of the cavity perpendicular to the longitudinal axis of the die and/or cavity. For example, referring again to FIG. 1F, die 140 comprises cavity 160 having a substantially circular cross-sectional shape. Non-limiting examples of suitable cross-sectional shapes include substantially circular (e.g., circular, substantially elliptical, capsule-like), substantially linear (e.g. thin lines or stripes), substantially polygonal (e.g., substantially triangular, substantially square, substantially rectangular, substantially trapezoidal, substantially hexagonal, or the like). In some cases, a cross-section of the cavity may be irregularly shaped. In some embodiments, a cross-section of the cavity is substantially round (as illustrated in FIG. 3B). Those skilled in the art would be capable of selecting suitable shapes for the cavity based upon tablet shapes as guided by the teachings of this specification.

As noted above, in some embodiments, the die comprises an opening. In some embodiments, the opening has a cross-section mated with the cross-section of the substrate. For example, the opening, in some cases, has a cross-section with substantially the same shape as the cross-section of the substrate. In certain embodiments, the cross-sectional dimension of the opening is the same as or substantially the same as (e.g., within 5% of) the cross-sectional dimension of the substrate. In some embodiments, the average distance, during operation, between the exterior surface of the substrate and the interior surface of the opening of the cavity may be less than or equal to about 3 mm, less than about 2 mm, less than about 1 mm, or less. To calculate the average distance between the exterior surface of the substrate and the interior surface of the opening, one would determine—at each point along the interior surface of the opening—the shortest distance between the interior surface of the opening at that point and the exterior surface of the substrate. The average distance would then be calculated as a number average.

In some embodiments, the interior surface of the opening of the cavity substantially conforms to the exterior surface of the substrate. For example, in some embodiments, the opening of the cavity has an interior contour that physically matches the exterior contour of the substrate. For example, in some embodiments, the opening of the cavity is threaded. In some such embodiments, the opening may be threaded and the substrate may be threaded such that the opening and substrate have matching threads.

Figure 4A:
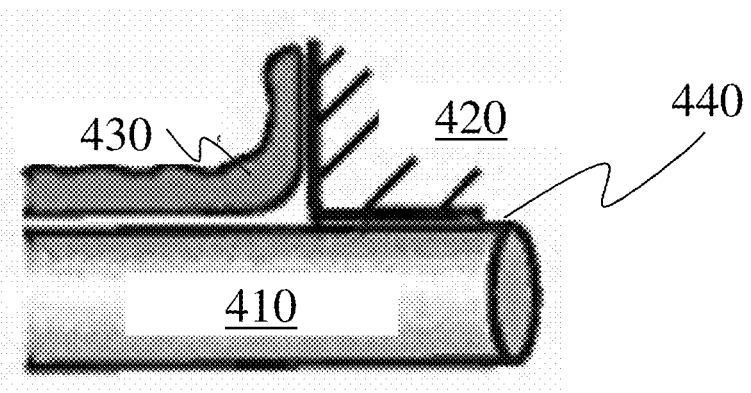
FIGS. 4A-4C are schematic diagrams of the raking angle for removing material from a substrate, according to one set of embodiments.
Figure 4B:
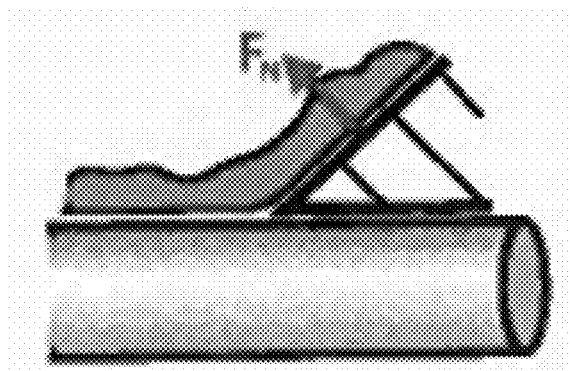
Figure 4C:
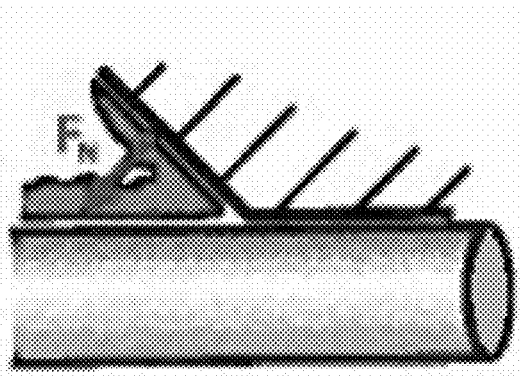

In some embodiments, the opening has a particular raking angle. The raking angle generally refers to the angle between the wall of the opening and the substrate. For example, as illustrated in FIG. 4A, in some embodiments, die 420 comprises opening 440 such that the raking angle (e.g., the angle at which material 430 will be removed from the substrate 410) between the substrate 410 and the die 420 is about 90 degrees. In some embodiments, the raking angle is less than about 90 degrees (FIG. 4B). In certain embodiments, the raking angle is greater than about 90 degrees (FIG. 4C).

The die itself may comprise any suitable material. Non-limiting examples of suitable die materials include metals, polymers, ceramics, composites thereof, and the like. According to certain embodiments, the die should be sufficiently mechanically strong to withstand the force applied during compaction of the material from which the tablet is made.

As described above, in some embodiments, after disassociating the material from the substrate, the material within the cavity may be compacted. In certain embodiments, the material within the cavity is compacted such that the material forms a tablet. In some embodiments, the material within the cavity may be compacted using a compaction plunger. In some embodiments, the compaction plunger has an exterior surface that substantially conforms to the interior surface of the cavity.

The compaction plunger may comprise any suitable material. Non-limiting examples of suitable die materials include metals, polymers, ceramics, composites thereof, and the like. According to certain embodiments, the compaction plunger should be sufficiently mechanically strong to withstand the force applied during compaction of the material from which the tablet is made. In some embodiments, the compaction plunger is a hydraulic press.

In some embodiments, the opening in the die is at least partially closed prior to the tablet being compacted within the cavity. For example, referring to FIG. 3A, in some embodiments, opening 350 is at least partially closed prior to compacting a tablet within cavity 330. In certain embodiments, after the substrate is passed through the opening, a closing material is deposited within the opening, filling the opening. The closing material may comprise any suitable material capable of filling the opening including, but not limited to, clay, metal, rubber, polymer, ceramic, combinations thereof, or the like. In some embodiments, the closing material should be sufficiently mechanically strong such that the material deposited within the cavity does not pass through the opening during compaction of the material. In some cases, the substrate may close the opening. For example, in some embodiments, the substrate is positioned such that the opening of the die is substantially closed, wherein the substrate is not present in the cavity of the die.

In some embodiments, the compaction plunger applies a particular force to the material such that the material forms a tablet.

In some embodiments, the force applied to compact the material is at least about 100 Newtons, at least about 196 Newtons, at least about 250 Newtons, at least about 500 Newtons, at least about 750 Newtons, at least about 1000 Newtons, at least about 1500 Newtons, at least about 2000 Newtons, at least about 4000 Newtons, or at least about 4900 Newtons. In certain embodiments, the force applied to compact the material is less than or equal to about 5000 Newtons, less than or equal to about 4900 Newtons, less than or equal to about 4000 Newtons, less than or equal to about 2000 Newtons, less than or equal to about 1500 Newtons, less than or equal to about 1000 Newtons, less than or equal to about 750 Newtons, less than or equal to about 500 Newtons, less than or equal to about 250 Newtons, or less than or equal to about 196 Newtons. Combinations of the above-referenced ranges are also possible (e.g., between about 100 Newtons and about 5000 Newtons, between about 196 Newtons and about 4900 Newtons). Other ranges are also possible.

In some cases, ambient temperature and composition (e.g. humidity) may be varied to control solidification of material before and/or during compaction.

The tablets described herein can, according to certain embodiments, be in the form of a small disk or cylinder of a compressed solid substance (e.g., the electrodeposited material). The material (e.g., the material to be tableted) may comprise any material suitable for electrodeposition. In some embodiments, the material is a fluid prior to electrodeposition. In certain embodiments, the material is dried. In some such embodiments, the material may be dried prior to compaction. In certain embodiments, the material may be dried after compaction. In certain embodiments, the material is suspended within (or in solution with) a fluid (e.g., a carrier fluid) prior to electrodeposition.

In some embodiments, the material to be deposited comprises an active pharmaceutical ingredient (API). In certain embodiments, the tablet comprising the material comprises an API. A variety of active pharmaceutical ingredients can be used in association with the systems and methods described herein. An active pharmaceutical ingredient may be any bioactive composition. In some embodiments, the active pharmaceutical ingredient (which can also be referred to as a "drug") can be an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005. In some embodiments, the active pharmaceutical ingredient may be selected from "Approved Drug Products with Therapeutic Equivalence and Evaluations," published by the United States Food and Drug Administration (F.D.A.) (the "Orange Book"). In some though not necessarily all embodiments, the active pharmaceutical ingredient is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present embodiments. In certain embodiments, the active pharmaceutical ingredient is a small molecule. Exemplary active pharmaceutical ingredients include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and/or prostaglandins.

Non-limiting examples of active pharmaceutical ingredients that can be used in association with the systems and methods described herein include acetaminophen, ibuprofen, acetylsalicylic acid (aspirin), albendazole (ABZ), famotidine (FAM), cromolyn sodium salt, mebendazole, carbamazepine, indomethacin, ketoprofen, chloramophenicol, ketoconazole, itraconazole, tetracycline hydrochloride, chlorotetracycline hydrochloride, amphotericin B, acyclovir, salicylic acid, nabumetone, naproxen, sulindac, ketanserin, clarithromycin, ferulic acid, rifampin, paclitaxel, doxorubicin hydrochloride, flufenamic acid, acetazolamide, piracetam, sulfamerazine, mefenamic acid, nitrofurantion, nifedipine, sulfathiazole, cefaclor, norfloxacin, cephradine, levodopa, methazolamide, nystatin, paromomycin sulfate phenelzine sulfate, piperazine citrate, baclofen, ceforanide, fenbendazole, mesalamine, norfloxacin, allantoin, azathioprine, carbidopa, cefadroxil, cephalexin, cephradine, codeine sulfate, dimethicone, epinephrine, furazolidone, gentamicin sulfate, iopamidol, lisinopril, magaldrate, reserpine, riboflavin, aliskiren, carbamazepine (CBZ), ibuprofen and its sodium salt, indomethacin, chloramphenicol, acetaminophen, ketoprofen, griseofluvin, fenofibrate, sorbitol, mannitol, propranolol, ranitidine, and/or caffeine.

In some cases, the material to be deposited and/or the tablet comprises a vitamin (such as those used for vitamin supplementation). Non-limiting examples of vitamins include vitamin A, vitamin C, vitamin E, vitamin K, folic acid, thiamine, niacin, pantothenic acid, vitamin $B_6$, biotin, and/or vitamin $B_{12}$.

In some embodiments, the material to be deposited and/or the tablet comprises an ingestible composition such as a food product. Non-limiting examples of such ingestible food products include sugar-based products (such as sugar crystals, hard candies, chewable candies), dehydrated vegetable pulp, dehydrated fruit pulp, pseudocereals (such as buckwheat, flax, chia, quinoa, sesame), cereals (such as barley, maize, oats, rice, rye, spelt, wheat, rice), nuts (such as acorns, almonds, cashews, hazelnuts, macadamias, pistachios, pine nuts, walnuts), legumes (such as chickpeas, peas, fava beans, peanuts, soybeans) including beans (such as coffee beans, castor beans, cocoa beans, vanilla beans), and combinations thereof.

Tablets comprising such ingestible food products may be useful, for example, for human consumption, as pet food, and/or vitamin supplementation.

The material to be deposited may be in particle form (e.g., a charged particle). In some embodiments, the material is in solution. The material (e.g., API, food product) may be added to the solution in particle form, e.g., directly from a purified sample, or may be first suspended in a carrier liquid. In some embodiments, organic (meaning carbon-containing) carrier liquids may be used to prepare suspensions of materials (e.g., APIs, food products) for electrospinning. While any carrier liquid generally useful to prepare a polymer solution may be used for preparation of the suspension, the fiber diameter, matrix pore size, and polymer structure may be influenced by the carrier liquid used to form the fibrous compositions. Examples of carrier liquids include, but are not limited to, water, ethanol, methanol, dimethylsulfoxide (DMSO), ethyl acetate, benzene, 2-butanone, carbon tetrachloride, n-heptane, n-hexane, cyclohexane, n-pentane, methylene chloride, dimethylformamide, chloroform, formic acid, ethyl formate, acetic acid, hexafluoroisopropanol, cyclic ethers, acetone, acetonitrile, p-cresol, toluene, xylene, mesitylene, diethyl ether, glycol, petroleum ether, hexamethyl-phosphoric triamide, pyridine, trimethylamine, picoline, $C_2$-$C_5$ alcohol acetates, 1-4 dioxane, tetrahydrofuran, dichloromethane, 1-propanol, 2-propanol, anisole, 1-butanol, 2-butanol, butyl acetate, tert-butyl methyl ether, cumene, ethyl ether, formic acid, heptane, isobutyl acetate, isopropyl acetate, methyl acetate, 3-methyl-1-butanol, methylethyl ketone, methyl isobutyl ketone, 2-methyl-1propoanol, pentane, 1-pentaanol, propyl acetate, N,N-dimethylacetamide (DMAC), and combinations thereof. In some embodiments, the carrier liquid is selected to be noncytotoxic.

In some embodiments, the material to be deposited is suspended in a polymer solution. The polymer solution generally comprises a polymer. In some embodiments, the polymer yields polymeric fibers during electrodeposition processes. Non-limiting examples of suitable polymers include polyurethane (meaning a thermoplastic polymer produced by the reaction of polyisocyanates with linear polyesters or polyethers containing hydroxyl groups), polyvinylidine fluoride, poly(lactic acid-glycolic acid), poly(lactic acid), poly(glycolic acid), a poly(orthoester), a poly (phosphazene), poly(caprolactone), a polyacrylamide, polyvinyl pyrrolidone, collagen, polyethylene oxide, polyacrylic acid, polyvinyl chloride, polystyrene, poly 1-lactide, poly methyl methacrylate, nylon 6,6, cellulose acetate, poly butyl methacrylate, poly 2-dimetyl aminoethyl, poly ethyl acrylate, poly trimethyl amino ethyl, poly methacrylate chloride, poly vinyl alcohol, methylcellulose, ethylcellulose, hydroxypropyl cellulose, hydroxyethyl cellulose, hydroxypropylmethyl cellulose, hydroxyethylmethyl cellulose, poly (D-lactide), poly (DL-lactide), polyglycolide, poly (DL-lactide-co-glycolyde), chitosen, carrageenan, poly(alginic acid), xanthan gum, gelatin, poly(sebacic acid), poly(adipic acid), poly(fumaric anhydride), poly (4,4'-stilbene dicarboxylic acid anhydride), and combinations thereof.

The ratio of material (e.g., API, food product) to polymer by weight may be between about 5% and about 10% in some embodiments, between about 10% and about 20% in some embodiments, between about 20% and about 40% in some embodiments, between about 40% and about 60% in some embodiments, between about 60% and about 80% in some embodiments, or between about 80% and about 100% in some embodiments. In some implementations, higher ratios may be used.

The materials and/or tablets described herein may be used in "pharmaceutical compositions" or "pharmaceutically acceptable" compositions, which comprise a therapeutically effective amount of one or more of the polymers or particles described herein, formulated together with one or more pharmaceutically acceptable carriers, additives, and/or diluents. The pharmaceutical compositions described herein may be useful for diagnosing, preventing, treating or managing a disease or bodily condition including conditions characterized by oxidative stress or otherwise benefitting from administration of an antioxidant. Non-limiting examples of diseases or conditions characterized by oxidative stress or otherwise benefitting from administration of an antioxidant include cancer, cardiovascular disease, diabetes, arthritis, wound healing, chronic inflammation, and neurodegenerative diseases such as Alzheimer Disease.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or tablet, involved in carrying or transporting the subject compound, e.g., from a device or from one organ, or portion of the body, to another organ, or portion of the body. Each carrier should, according to certain embodiments, be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, a "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, certain of the embodiments described herein are directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition.

The following examples are intended to illustrate certain embodiments of the present invention, but do not exemplify the full scope of the invention.

Example 1

The following examples demonstrates the determination of parameters of an exemplary system for electrodeposition of a material onto a substrate, according to certain embodiments.

This example generally involves electrospinning a solution of polyvinylpyrrolidone (PVP) and pure ethanol to various collector embodiments. A solution of 8 wt % 1.3 MDa PVP (Sigma Aldrich) and ethanol was used in Example 1. After the formulation was prepared, a syringe was filled with solution, and flexible polyurethane tubing was connected between the syringe and the back of an emitter. A spinneret was used at the emitter. Any air in the syringe was expelled, and solution was manually propelled into the tubing. The syringe was then loaded into the syringe pump. The experimental setup was checked to ensure that the spinneret was attached to the high voltage power supply and that the collector was grounded. The pump was run until dripping was observed from the needle tip and then the power supply was turned on and a specified voltage was applied to the spinneret. Electro spinning proceeded for a specified length of time until a desired volume of material had been spun and then power was shut off to the system.

The spinning solution was prepared in advance of experimental trials as close to the actual experiment run as possible, in order to minimize solution aging. Since ethanol solvent is generally volatile at room temperature and can quickly evaporate, care was taken to prevent evaporation and maintain relatively constant solution properties. The formulations used in experimental trials were specified by the weight percent of each of constituent ingredients. To produce the actual solution, dry solid constituents were first individually weighed and then added to a dry clean flask. The flask was placed on a scale (Ohaus SP202 AM), which was then tared, and the liquid solvent was added until the prescribed solvent mass was achieved. A magnetic stir bar was added to the flask, and the solution was mixed on a stir plate (VWR 7×7 CER Hotplate/Stirrer) for at least 15 minutes. Stirring times were extended for solutions containing higher percentages of solute. Higher-viscosity solutions which retained small air bubbles after stirring were subjected to a degassing procedure in an ultrasonic water bath (Bransonic Ultrasonic Cleaner 8510R-MT). An example solution recipe can be found in Table 1.

TABLE 1

Example of a solution recipe.

| Solution by Polymer Mass | |
|---|---|
| Concentration (wt %) | 8.00% |
| Polymer | 1.3 MDa PVP |
| Mass Dry Polymer (g) | 5.00 |
| Polymer Molecular Weight (g/mol) | 1,300,000 |
| Solvent | Ethanol |
| Mass Solvent (g) | 57.5 |
| Solvent Density (g/mL) | 0.789 |
| Volume Solvent (mL) | 72.88 |
| Solution Recipe | |
| Mass Dry Polymer (g) | 5 |
| Volume Solvent (mL) | 72.88 |

Thin liquid jetting generally occurs when electrostatic forces overcome surface tension effects. In order to develop a range of parameter values for later testing of electrospinning performance, it was desirable to know the critical spinning voltage of the experiment setup. Theory points to the critical voltage as a function of spinneret-collector (SC) gap distance, since Coulomb's Law maintains that the electrostatic force between two charges is proportional to $1/r^2$, where r is the gap distance. Thus decreasing the gap distance may also decrease the critical spinning voltage above which spinning begins.

Initial electrospinning trials at various voltages and SC gap distances had identified an SC gap distance of 300 mm as an distance which produced dry fibers at an applied voltage of 30 kV, while still allowing higher voltages to be tested by the 50 kV experimental power supply. Utilizing these values as starting points, two sets of experiments were run. The first tested the theory that critical spinning voltage increased with gap distance. Electrospinning trials were run at a range of SC gap distances from 150 mm to 300 mm, with an experimental solution flow rate of 0.5 mL/min. The applied voltage at which a stable Taylor cone was established was recorded for each gap distance. The collector rod was cleaned of deposited fibers and liquid solution between runs, in order to eliminate any electrically insulating effects these might have on the system. The second set of trials focused on the identified 300 mm gap distance and tested whether the system solution flow rate had any influence on the critical spinning voltage. The SC gap for these experiments was held at 300 mm and the critical electrospinning voltage was recorded for flow rates of 0.5, 1.0, and 1.5 mL/min.

Initial experiments indicated that a horizontal static rod (HSR) collector design might yield good spinning productivity. An arbitrarily long rod was not selected in certain cases because rod droop may become a factor with increasing length. Droop can be calculated from the physical dimensions of the rod and added weight from spun material to determine deflection of the rod. In some cases, the system was adjusted such that this deflection remained a relatively insignificant proportion of the total electrode collector distance, in order to maintain uniform electric fields. A two factorial experiment design was run to determine sets of stable system operating parameters for an HSR collector. The two tested parameters were the applied electrode voltage and the system solution flow rate. The collector rod was kept static during the experiments to ensure that electrospinning results for the setup were a function the particular voltage and flow rate values tested. Trials were run at flow rates of 0.5, 1.0 and 1.5 mL/min and applied voltages of 30, 40 and 50 kV. Experiments were designed to produce a 0.2 g tablet for all experimental trials. Run times were calculated based on the flow rate used and are detailed in Table 2.

TABLE 2

Summary of experimental run times.
Timer Chart 0.2 g pill
Formulation 8 wt % 1.3 MDa PVP + ETOH

| Flowrate (mL/min) | Timer (min) | Timer display |
|---|---|---|
| 0.5 | 5.00 | 5:00 |
| 1 | 2.50 | 3:00 |
| 0.75 | 3.33 | 3:20 |
| 1.5 | 1.67 | 1:40 |

Figure 6:
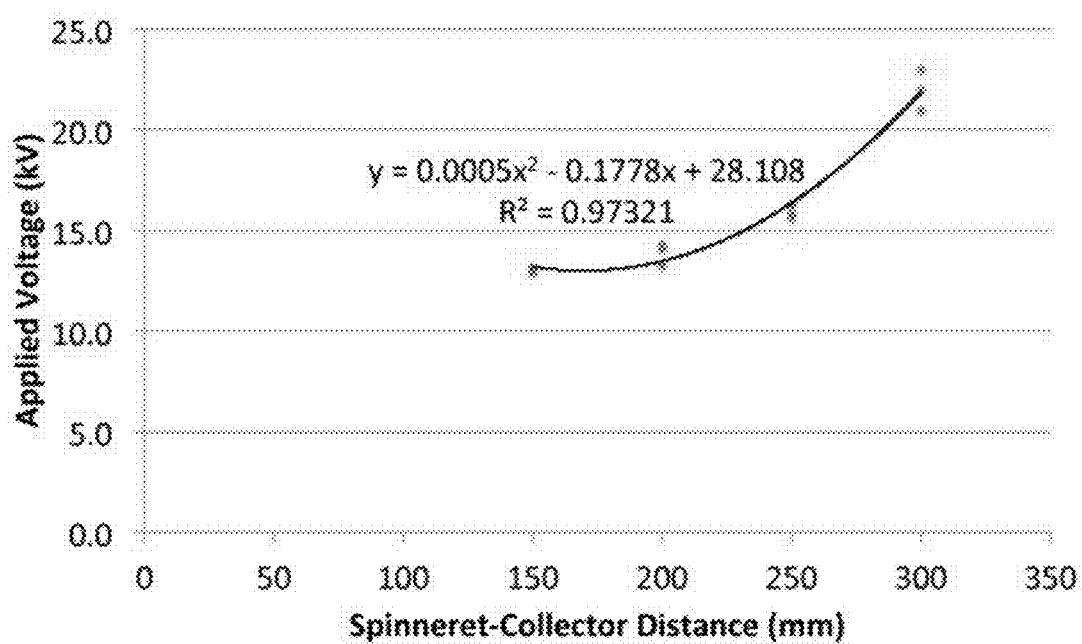
FIG. 6 is a plot of applied voltage versus source-substrate distance, according to one set of embodiments.

Experiments were run to characterize the critical spinning voltage of the process, above which jetting could occur from the spinneret. This was tested with the same physical setups as later horizontal rod spinning experiments in Example 1. The critical spinning voltage characterizations were performed to test whether variations in the solution flow rate or system spinneret-collector (SC) gap distance changed the voltage needed to initiate jetting from the spinneret. The electrostatic force between two charges is generally described by Coulomb's Law, where electrostatic force is proportional to the product of the charges divided by the distance between the charges, squared. For any set of constant charges, the electrostatic force is generally proportional to the inverse square of the distance between them. A simple experiment was run to confirm this relationship, testing the effect of the distance between the spinneret and collector on the critical applied voltage required to induce spinning. At each SC distance tested, solution was pumped through the system at a constant flow rate of 0.5 mL/min, while the voltage applied to the spinneret was increased until visually stable jetting occurred. The results are shown in FIG. 6. The applied voltage to produce the same electrostatic force increased proportionally to $r^2$ as the spinneret-collector (SC) gap distance was increased. The data supports a $1/r^2$ relation between electrostatic force and SC distance.

Figure 7:
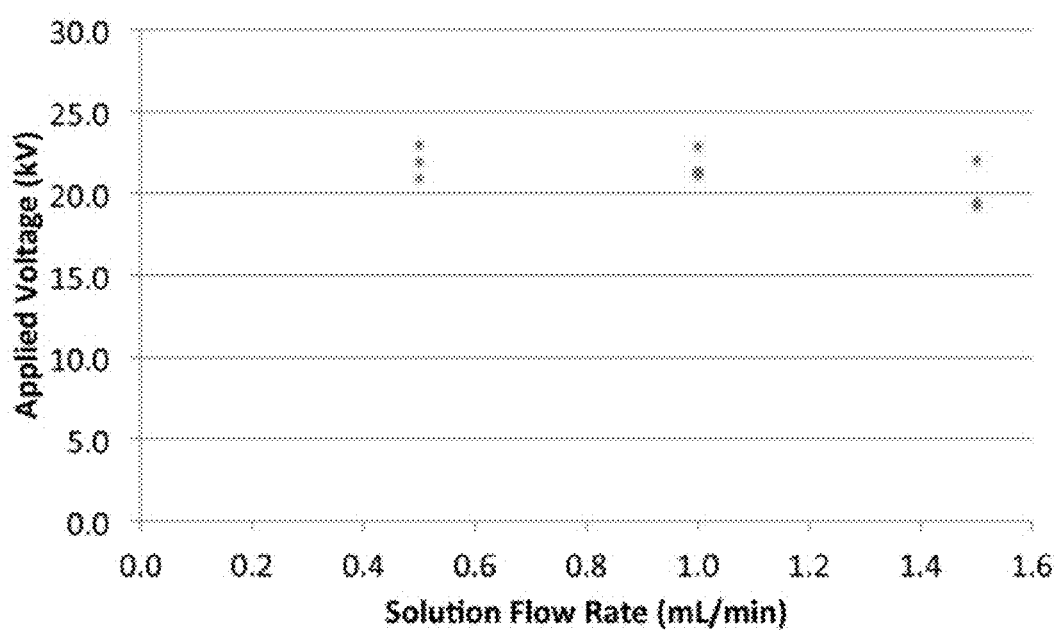
FIG. 7 is a plot of applied voltage versus solution flow rate, according to one set of embodiments.

Since Coulomb's Law does not account for surface tension and gravity, the effect of flow rate variation on the critical spinning voltage was also tested. For a range of flow rates from 0.5 to 1.5 mL/min, the applied voltage was again increased until jetting occurred, at a constant SC distance and flow rate. The results are plotted in FIG. 7. As can be observed in FIG. 7, there was relatively little significant difference in the critical spinning voltage over the range of flow rates utilized.

The horizontal static rod (HSR) experiments tested the spinning performance of a range of experimental flow rates ranging from 0.5 mL/min to 1.5 mL/min and applied voltages of 30 kV to 50 kV, all with a SC distance of 300 mm. These results, under the particular conditions outlined in Example 1, found that for a SC distance of 300 mm there was a unique parameter combination of 0.5 mL/min flow rate and 40 kV applied voltage which was capable of spinning the desired pill mass. A flow rate of 0.5 mL/min and 30 kV and 50 kV applied voltages produced a good initial spin, but wet spots before the end of the process. For a flow rate of 1.0 mL/min, wet spots were also observed at 40 kV and 50 kV applied voltages, and incomplete drying was observed at 30 kV. For a flow rate of 1.5 mL/min, incomplete drying was observed at applied voltages of 30 kV to 50 kV.

The HSR collector generally produced an asymmetric circumferential distribution of spun fiber material around the rod. Such asymmetric distribution is not desirable in certain applications, but can be addressed, for example, by rotating the substrate onto which the material is deposited, as described in Example 2.

Example 2

The following example demonstrates the deposition of material onto an elongated rod, according to an exemplary embodiment.

Using the parameters described in Example 1 for a flow rate of 0.5 mL/min, system performance was then tested while the collector rod was rotated at approximately 300 RPM. The experimental procedure was the same as for Example 1, with the exception that collector rotation was initiated before solution was pumped through the system. The finished spinning results were compared to results of Example 1 using the same parameters but with a static collector.

A final electrospinning experiment was performed to test whether multiple needles could be used in the setup to increase the bulk flow rate of the system, since experimental evidence suggested that a single needle of any given diameter has an upper bound on the flow rate it can successfully electrospin. Thus, to push the bulk flow rate past this point, multiple jets were used. Two needles were used in the experiment, spaced 200 mm from each other, and each attached to the fluid loop with the same length of tubing to eliminate pressure head differences. The multi-needle experiments attempted to electro-spin at two different SC distances, 300 mm and 250 mm and at 40 kV and 20 kV applied voltage respectively. The collector was again rotated at 300 RPM.

Free surface electrospinning was performed with three different solutions:

Solution (A): 30 wt % 55 kDa PVP (Sigma Aldrich) in ethanol.

Solution (B): 7 wt % (146-186) kDa PVA in water.

Solution (C): 20 wt % (4-88) MoWiol and 1.5 wt % (146-186) kDa PVA in water and 21.5 wt % Fenofibrate.

After the formulations were prepared, a reservoir of approximate volume 30 ml was filled with each of these solutions in three separate experiments. The spinneret used was a wire electrode in which several thin metal wire electrodes were stretched tightly between two Teflon wheels separated by a certain distance and mounted on a threaded rod to form a rotating spindle. The parallel wires running across the two wheels were separated by the distance of grooves cut on the wheels. The spinneret was connected to a high voltage power supply. The wires on the spinneret get coated with the liquid in the bath as the spindle rotates along its axis. The liquid coating then formed several droplets on the wires due to Plateau-Rayleigh instability. Upon application of high voltage, these droplets deformed and generated liquid jets which then got stretched under the application of electric field. The solvent evaporated as the jets travelled to the collector. The collector was a horizontal static metal rod. The applied electric potential, distance and field for solution A, B and C were: 35 kV, 21 cm, 1.4 kV/cm, 40 kV, 26 cm, 1.53 kV/cm and 45 kV, 26 cm, 1.73 kV/cm respectively. Spinning for 15 mins produced enough electrospun material to generate tablets of 75 mg.

Figure 8A:
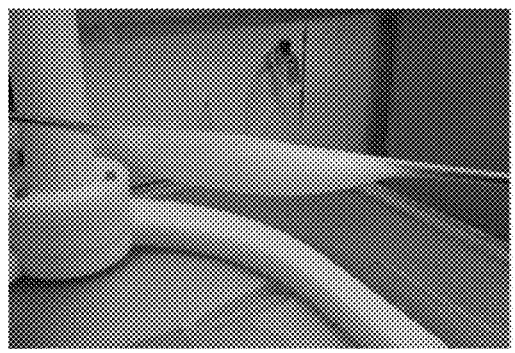
FIGS. 8A-8B are photographs of material deposited on a substrate, according to one set of embodiments.
Figure 8B:
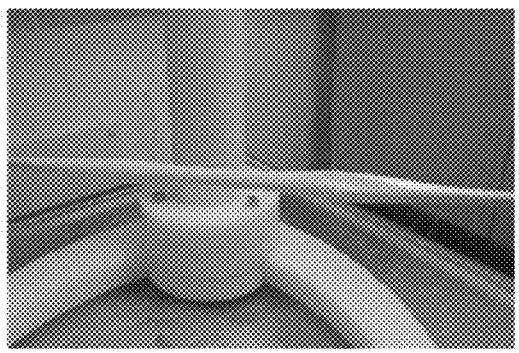

The experimental results of electrospinning at the successful HSR flow rate of 0.5 mL/min, applied voltage of 40 kV and SC distance of 300 mm were then compared to experimental results using a setup with the same parameters, with the addition rotating the collector rod at 300 RPM. The results of the rotating rod experiments show a vast improvement in circumferential uniformity of the fiber distribution as compared with the HSR results. The uniformity of deposition may result from at least two phenomena: first, the rotation may cause the rod surface area to see equal time facing the spinning needle, and second, any long fiber sections which tended to drape over the collector rod in the HSR experiments may have been rolled up onto the rod in a manner similar to a retracting winch. The two combined factors contributed to the more compact and uniform distribution (FIG. 8B) as compared to the HSR results (FIG. 8A).

Example 3

The following example demonstrates the removal of the material from an elongated rod, according to an exemplary embodiment.

If the electrospinning process in any horizontal collector rod experiment was successful, and no liquid solution was observed on the collector, the rod was manually pulled through a 12 mm diameter tableting die. The collector rod was constructed from a tight tolerance, O1 tool steel, 3.76 mm+/−0.01 mm (0.1480 in.+/−0.0005 in. nominal) diameter rod, that formed a tight clearance fit with a type 316 stainless steel 3.96 mm (0.156 in.) ID washer acting as the stripper plate. This resulted in an approximately 100 micron gap between the rod and stripper plate. A cross section of the tablet forming die is should in FIG. 3A.

Figure 5:
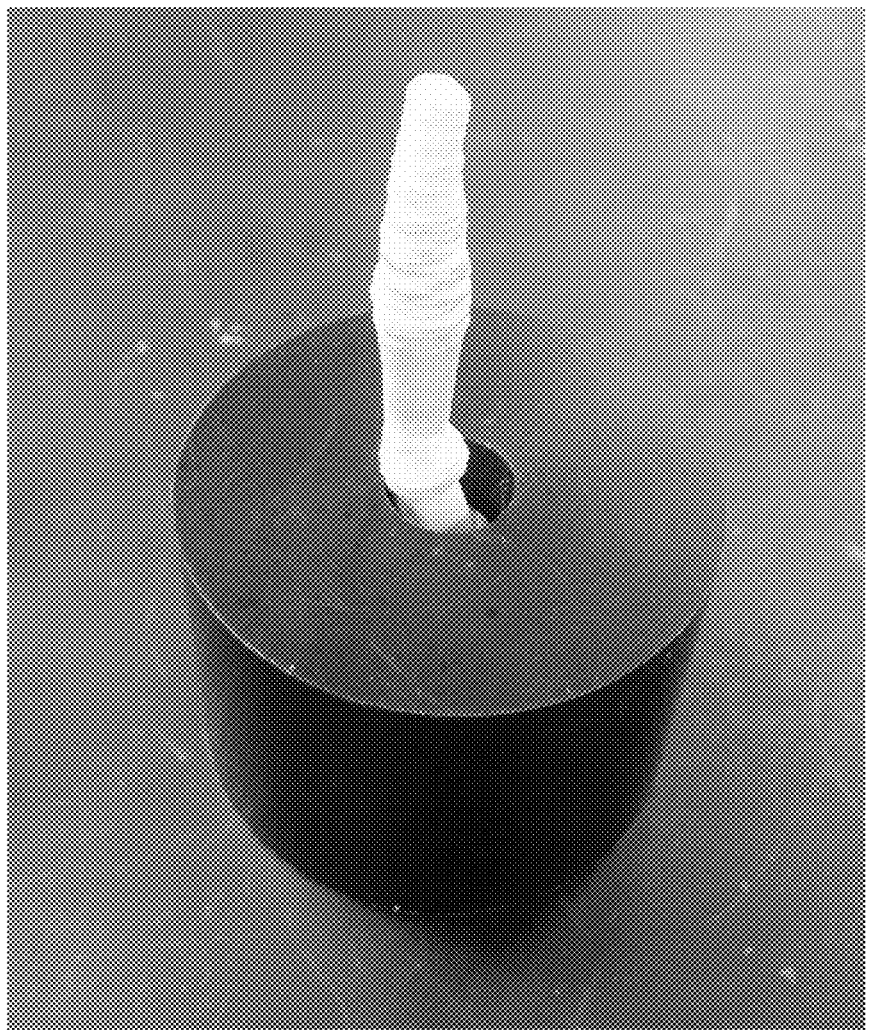
FIG. 5 is a photograph of removed material deposited in a cavity, according to one set of embodiments.

Stripping was performed of deposited material that included properly spun fibers. In some cases, material that had been deposited as a liquid, and subsequently dried, adhered to the collector rod and tended to jam in the clearance gap between the stripper plate and the rod. The stripped material tended to maintain its integrity as a continuous mat post-strip and, as can be seen in FIG. 5, formed a compressed tube-like structure which often projected out past the die orifice. The collector rod was also examined visually post-strip to ensure that a reliable, clean strip had occurred. This observation, in conjunction with the observed quality of the spun fibers, can be used to determine characteristics of different spinning qualities to be correlated with strip quality.

Example 4

The following example demonstrates the compression of the material removed from an elongated rod, according to an exemplary embodiment.

At the conclusion of the stripping procedure, the test die was filled with the fiber tube removed from the collector. A die plug was manually inserted into the bottom of the tableting die to form a uniform flat die floor. The entire die assembly was then placed into the tableting die, and a compression trial run. The tableting die was equipped with a 500 kg load cell and set in all experiments to perform continual compression on the material in the die until a load measurement of 400 kg was reached. Due to the measurement lag, this generally resulted in a maximum compression force of around 420 kg. Once the plunger reached the die post-peak load, the finished tablet could be ejected and its mass measured.

Figure 9:
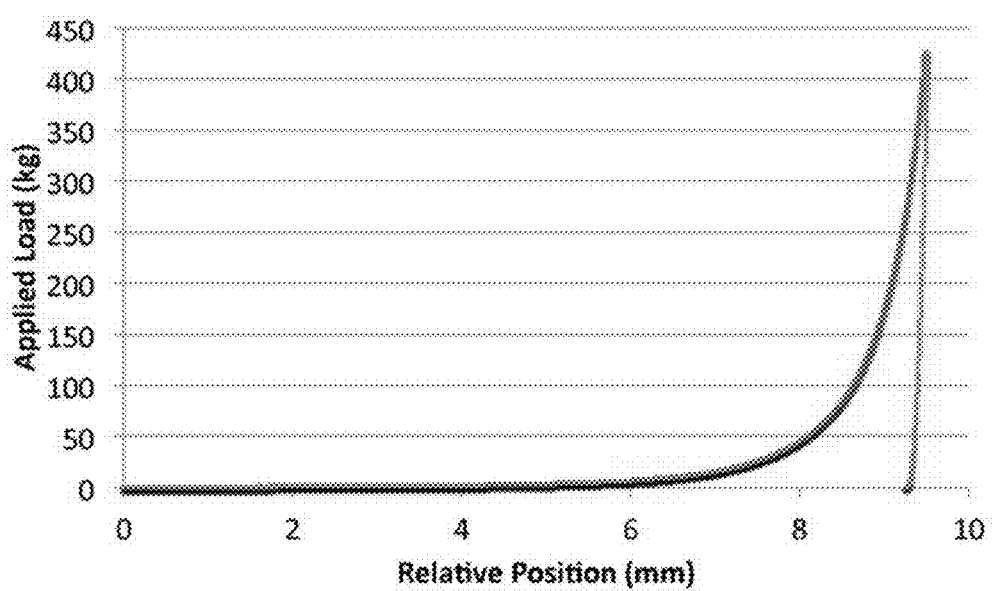
FIG. 9 is a plot of applied load versus relative position, according to one set of embodiments.

The compression process yielded results which signaled a non-uniform radial distribution of material in the die. Compression results from the HSR collector also demonstrated that in the HSR trials, there was a non-uniform circumferential distribution of material as well, which was expected since the collector did not see a uniform distribution of deposited fiber material around its long axis. Compression data from the tablet press was very similar across all compression trials, and an example plot from one of the HSR experiments is found in FIG. 9.

The load cell measured average force across the tablet being produced, but visually, it was clear that higher compaction pressures built up near the center of the die floor, while near the die walls less force was transferred. This problem may likely have been solved by an increase in material volume in the die. The final 0.2 g tablets had an average thickness of 1.9 mm, which resulted in a thickness to diameter ratio of just under 1:6. The fiber material did not seem to flow sufficiently under compressive pressure to fill the die to its edges—rather, the material appeared to remain mostly locally stationary, with larger compressive pressures building up in areas of greater fiber distribution around the center of the die floor. A larger volume of material in the die would generally allow more material to redistribute itself earlier on in the compression process, resulting in a more homogeneous tablet.

Figure 10:
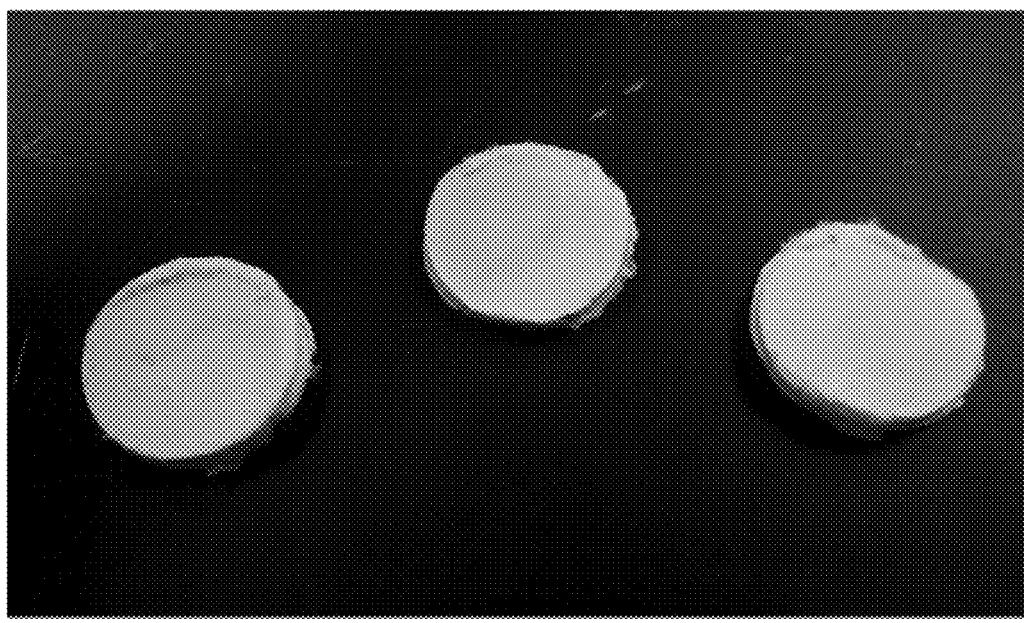
FIG. 10 is a photograph of tablets produced by an exemplary system, according to one set of embodiments.

The compression process did appear to be robust and repeatable as shown in FIG. 10, in which nearly identical tablets were produced from a variety of different flow rates and spinning voltages.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, eliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. An electrodeposition system for manufacturing a tablet, comprising:

a substrate having a first electric potential;

a source configured to contain a fluid, the source having a second electric potential different than the first electric potential;

an emitter associated with the source and configured to emit fluid contained within the source toward the substrate;

a die comprising a cavity and an opening, the die configured to strip material from an exterior surface of the substrate when the die and the substrate are moved relative to each other; and an actuator associated with the substrate and/or the die and configured to move the die and the substrate relative to each other, wherein the substrate can extend through the cavity and the opening of the die such that the die circumscribes the substrate when the die and the substrate are moved relative to each other by the actuator.

2. A system as in claim 1, wherein the substrate comprises an elongated rod.

3. A system as in claim 1, comprising a plunger that fits into the cavity of the die and a compaction actuator configured to move the plunger into and/or out of the cavity of the die.

4. A system as in claim 3, wherein the plunger has an exterior surface that conforms to an interior surface of the cavity.

5. A system as in claim 3, wherein the plunger is configured to apply a force of at least about 100 Newtons.

6. A system as in claim 1, wherein the system comprises an electric potential generator electrically connected to the substrate and the source.

7. A system as in claim 1, wherein the substrate has an exterior surface comprising protrusions.

8. A system as in claim 7, wherein the protrusions of the exterior surface of the substrate are configured to mate with protrusions on an exposed surface of the die.

9. A system as in claim 7, wherein the protrusions of the exterior surface of the substrate are substantially helical.

10. A system as in claim 1, wherein the source comprises a reservoir.

11. A system as in claim 1, wherein the source comprises a mixing rod.

12. A system as in claim 1, wherein the cavity comprises a wall that facilitates the removal of the material from the substrate and the deposition of the material in the cavity.

13. A system as in claim 1, wherein a cross-sectional dimension of the opening is within 5% of a cross-sectional dimension of the substrate.

14. A system as in claim 1, wherein an interior surface of the opening conforms to the exterior surface of the substrate.

15. A system as in claim 1, wherein an average distance, during operation, between the exterior surface of the substrate and an interior surface of the opening is less than or equal to about 3 mm.

16. A system as in claim 1, comprising a closing material configured to fill the opening of the die.

17. A system as in claim 1, wherein the actuator is capable of both rotating the substrate and moving the substrate in a linear direction.

18. A system as in claim 1, wherein the die circumscribes the substrate.

* * * * *